US010857185B2

(12) United States Patent
Deng et al.

(10) Patent No.: US 10,857,185 B2
(45) Date of Patent: Dec. 8, 2020

(54) COMPOSITIONS AND METHODS FOR REPROGRAMMING NON-NEURONAL CELLS INTO NEURON-LIKE CELLS

(71) Applicants: Beihao Stem Cell and Regenerative Medicine Research Institutes Co., Ltd., Guangdong (CN); Peking University, Beijing (CN)

(72) Inventors: Hongkui Deng, Beijing (CN); Xiang Li, Beijing (CN); Xiaohan Zuo, Beijing (CN)

(73) Assignees: Beihao Stem Cell and Regenerative Medicine Research Institutes Co., Ltd., Guangdong (CN); Peking University, Beijing (CN)

( * ) Notice: Subject to any disclaimer, the term of this patent is extended or adjusted under 35 U.S.C. 154(b) by 150 days.

(21) Appl. No.: 15/741,204

(22) PCT Filed: Jul. 1, 2016

(86) PCT No.: PCT/CN2016/088082
§ 371 (c)(1),
(2) Date: Dec. 29, 2017

(87) PCT Pub. No.: WO2017/005136
PCT Pub. Date: Jan. 12, 2017

(65) Prior Publication Data
US 2018/0193386 A1 Jul. 12, 2018

(30) Foreign Application Priority Data
Jul. 3, 2015 (CN) .......................... 2015 1 0387877

(51) Int. Cl.
C12N 5/00 (2006.01)
A61K 35/30 (2015.01)
A61K 9/00 (2006.01)
C12N 5/074 (2010.01)
C12N 5/0793 (2010.01)

(52) U.S. Cl.
CPC ............ A61K 35/30 (2013.01); A61K 9/0019 (2013.01); C12N 5/0607 (2013.01); C12N 5/0619 (2013.01); C12N 2501/01 (2013.01); C12N 2501/115 (2013.01); C12N 2501/13 (2013.01); C12N 2501/15 (2013.01); C12N 2501/60 (2013.01); C12N 2501/727 (2013.01); C12N 2501/999 (2013.01); C12N 2502/086 (2013.01); C12N 2503/02 (2013.01); C12N 2506/08 (2013.01); C12N 2506/1307 (2013.01); C12N 2506/1353 (2013.01); C12N 2506/1369 (2013.01); C12N 2506/1384 (2013.01); C12N 2506/1392 (2013.01)

(58) Field of Classification Search
CPC ....................... C12N 5/0619; C12N 2501/999
See application file for complete search history.

(56) References Cited

FOREIGN PATENT DOCUMENTS

| WO | WO 2012/118988 A1 | 9/2012 | |
|----|----|----|----|
| WO | WO 2012/118988 A8 | 9/2012 | |
| WO | WO 2015/041809 A3 | 3/2015 | |
| WO | WO 2015041809 * | 3/2015 | ............... C12N 5/00 |
| WO | WO-2015041809 A2 * | 3/2015 | ............... C12N 5/00 |

OTHER PUBLICATIONS

Li et al. Cell Stem Cell 17:195-203, Aug. 6, 2015. (Year: 2015).*
Petrik et al. The FASEB Journal 26:3148-3162, 2012 (Year: 2012).*
Scheider et al. Nature Chemical Biology 4(7):408-410, 2008 (Year: 2008).*
Janghwan Kim et al: "Direct lineage reprogramming to neural cells", Current Opinion in Neurobiology, vol. 22, No. 5, Oct. 2012 (Oct. 2012), pp. 778-784, XP009509244, ISSN: 0959-4388.
J. Kim et al: "Direct reprogramming of mouse fibroblasts to neural progenitors", Proceedings of the National Academy of Sciences, vol. 108, No. 19, May 10, 2011 (May 10, 2011), pp. 7838-7843, XP055027748, ISSN: 0027-8424, DOI: 10.1073/pnas.1103113108, p. 7842, col. 1, paragraph 1.

* cited by examiner

Primary Examiner — Marcia S Noble
(74) Attorney, Agent, or Firm — Ya-Fen Chen

(57) ABSTRACT

Cocktails of chemical inducers of neuron-like properties (CINP) is provided, which includes cAMP agonists, neurogenic small molecules, glycogen synthase kinase inhibitors, TGFβ receptor inhibitors, and BET family bromodomain inhibitors and optionally, a selective inhibitor of ROCK or p38 MAPK. These cocktails are used in a method of inducing neuron-like properties in partially or completely differentiated non-neuronal cells. The method includes contacting cells of a first type (non-neuronal) with the CINPs for a sufficient period of time to result in reprogramming the cell into cells of a second type having neuron-like characteristics (CiNs). Isolated chemically induced neurons (CiNs) can be used in a number of applications, including but not limited to cell therapy.

14 Claims, 16 Drawing Sheets

COMPOSITIONS AND METHODS FOR REPROGRAMMING NON-NEURONAL CELLS INTO NEURON-LIKE CELLS

CROSS-REFERENCE TO RELATED APPLICATIONS

This application claims benefit of Chinese Application No. 201510387877.5 filed on Jul. 3, 2015.

FIELD OF THE INVENTION

The invention is generally directed to small molecule compositions and method for reprogramming non-neuronal eukaryotic cells into neuron-like cells.

BACKGROUND OF THE INVENTION

Direct lineage reprogramming has emerged as a promising, fast and direct approach for manipulating cell fate, which bypasses the teratoma risks associated with pluripotent stem cells. Fibroblasts can be directly converted into diverse functional cell types, including neurons, cardiomyocytes, hepatocytes and others, by the viral introduction of known cell-fate-determining transcription factors or microRNAs (Davis, et al., *Cell*, 51:987-1000 (1987); Huang, et al., *Nature*, 475:386-389 (2011); Ieda, et al., *Cell*, 142:375-386 (2010); Pang, et al., *Nature*, 476:220-223 (2011); Qian, et al., *Nature*, 485:593-598 (2012); Sekiya and Suzuki, *Nature*, 475:390-393 (2011); Szabo, et al., *Nature*, 468:521-526 (2010); Vierbuchen, et al., *Nature*, 463:1035-1041 (2010); Xue et al., *Cell*, 152:82-96 (2013); Yoo, et al., *Nature*, 476:228-231 (2011); Zhou, et al., *Nature*, 455:627-632 (2008); Du, et al., *Cell Stem cell*, 14:394-403 (2014); Huang, et al., *Cell Stem Cell*, 14:370-384. (2014); and Xu, et al., *Cell Stem Cell*, 16:119-134 (2015)).

However, the low efficiency of induction, the technical challenges and the genomic integration of the viral vectors used for direct reprogramming have raised concerns regarding its future use.

It is an object of the present invention to provide small molecules which induce/confer neuron-like properties to non-neuronal cells.

It is also an object of the present invention to disclose a method of inducing/conferring neuron-like properties to non-neuronal cells.

It is still an object of the present invention to provide chemically induced neurons.

It is a further object of the present invention to provide therapeutic compositions including chemically induced neurons.

It is also an object of the present invention to provide a method of treating and/or ameliorating neurodegenerative or neurological disorders, or neuronal injuries.

SUMMARY OF THE INVENTION

Small molecule cocktails have been identified which can be used to reprogram partially or completely differentiated non-neuronal cells into a neuron-like cell. Chemical compounds that induce/confer neuron-like properties (herein after, CINPs) to non-neuronal cells include the following molecules in an effective amount to induce/confer neuron-like properties in non-neuronal cells: 1) a cyclic adenosine monophosphate (cAMP) agonist, (2) a neurogenic small molecule, (3) a glycogen synthase kinase (GSK) inhibitor, (4) a transforming growth factor β (TGF β) inhibitor, (5) a BET family bromodomain inhibitor, and combinations thereof. Preferred cAMP agonists include rolipram, DBc-AMP (dibutyryl-cAMP), 8-bromo-cAMP and forskolin ("F"). In a more preferred embodiment, the cAMP agonist is forskolin. A preferred neurogenic small molecule is ISX9 ("I") [N-cyclopropyl-5-(2-thienyl)-3-isoxazolecarboxamide]. Preferred GSK inhibitors include CHIR99021 ("C") having the chemical name [6-[[2-[[4-(2,4-dichlorophenyl)-5-(5-methyl-1H-imidazol-2-yl)-2-pyrimidinyl]amino]ethyl]amino]-3-pyridinecarbonitrile]; SB216763 having the chemical name [3-(2,4-dichlorophenyl)-4-(1-methyl-1H-indol-3-yl)-1H-pyrrole-2,5-dione)]; GSK 3I XV; and Bio-acetoxime, having the chemical name [(2'Z,3'E)-6-bromoindirubin-3'-acetoxime]. A more preferred GSK inhibitor is CHIR99021. A preferred TGF β inhibitor is SB431542 ("S") having the chemical name [4-[4-(1,3-benzodioxol-5-yl)-5-(2-pyridinyl)-1H-imidazol-2-yl]benzamide]. Preferred BET family bromodomain inhibitors include I-BET151 ("B") having the chemical name [(7-(3,5-dimethylisoxazol-4-yl)-8-methoxy-1-((R)-1-(pyridin-2-yl)ethyl)-1H-imidazo[4,5-c]quinolin-2(3H)-one]; JQ1 having the chemical name [(6S)-4-(4-chlorophenyl)-2,3,9-trimethyl-6H-thieno[3,2-J][1,2,4]triazolo[4,3-a][1,4]diazepine-6-acetic acid 1,1-dimethylethyl ester]; bromosporine; and I-CBP112 having the chemical name [1-[7-(3,4-dimethoxyphenyl)-9-[[(3S)-1-methylpiperidin-3-yl]methoxy]-2,3,4,5-tetrahydro-1,4-benzoxazepin-4-yl]propan-1-one]. A more preferred BET family bromodomain inhibitor is I-BET151. The CINPs can be used alone or in combination (i.e., a cocktail) to induce/confer neuronal characteristics to non-neuronal cells. In one embodiment, a preferred cocktail of CINPs includes FICS; F in a concentration range from 50 to 100 µM; I in a concentration range from 10 to 20 µM; C in a concentration range from 10-20 µM and S in a concentration range from 2-10 µM. In other embodiments, the cocktail of CINPs includes FICB; FIC in the same concentration ranges disclosed for FICS, and B in a concentration range from 2-10 µM. The FICB cocktail optionally includes a selective inhibitor of Rho-associated, coiled-coil containing protein kinase (ROCK), for example, Y27632 [(+)-(R)-trans-4-(1-aminoethyl)-N-(4-pyridyl)cyclohexanecarboxamide+++dihydrochloride)] or a p38 MAPK inhibitor.

Also disclosed are chemically induced neurons (CiNs) that are neuron-like, morphologically and functionally. CiNs are not naturally occurring neurons. However, they are identified as CiNs based on characteristics selected from: (i) a morphology characteristic of neurons, for example, neurite outgrowth; (ii) expression of specific markers such as TUJ1 (Neuron-specific class III beta-tubulin), MAP2 (microtubule associated protein 2), NF-H (neurofilament H) and NeuN (Neuronal Nuclei); (iii) membrane properties exhibited by neurons, for example, excitatory or inhibitory membrane properties are evidenced by expression of vGlut (vesicular glutamate transporter) and/or Gad (glutamate decarboxylase) 67; and (iv) membrane depolarization, as measured in a patch-clamp assay, or combinations thereof. In addition, the CiNs show downregulation of genes characteristic of the lineage from which they are obtained. For example, when obtained from fibroblasts, CiNs show down-regulation of fibroblast hallmark genes such as Fap (fibroblast activation protein, alpha), Des (desmin), Slug (zinc finger protein SNAI2), Dcn (decorin), FSp1 (fibroblast specific protein 1), Collagen 1 and Twist2 (twist related protein 2, protein also known as class A basis helix-loop-helix protein 39). The CiNs can be included in a pharmaceutically acceptable carrier for treating, preventing, and/or ameliorating neurodegenerative or neurological disorders or neuronal injuries in a subject in need thereof.

Also disclosed is a method of reprogramming a non-neuronal cell into a neuron-like cell. The method includes providing a first cell that is not a neuron, and culturing the first cell in a normal (i.e., not supplemented with reprogramming small molecules) cell culture medium suitable for that cell type for a period of one to two days, preferably, 2 days. The cells are then transferred into an induction medium which includes a cocktail of CINPs for a time period effective to induce/confer one or more neuron-like properties in the cell, preferably between 14 and 24 days. For example, the cells can be cultured in induction medium for 14, 15, 16, 17, 18, 19, 20, 21, 22, 23 or 24 days. Where the cells of the first type are fibroblasts for example, the cells are grown in induction medium for about 20 days.

Following culture in induction medium, the cells are cultured in maturation medium for at least 10 days, preferably, for a period greater than 10 days. For example, the cells can be cultured in maturation medium for 10, 11, 12, 13, 14, 15, 16, 17, 18, 19, 20, 21, 22, 23, 24, 25, 26, 27, 28, 29 or 30 days, following which, cells of a second type (i.e., CiNs) are obtained. In a preferred embodiment, the cells are cultured in maturation medium for a period between 14 and 21 days. In this step, cells are preferably replated in maturation medium, in combination with primary astrocytes, following which CiNs are obtained.

Also disclosed is a method of treating for treating, preventing, and/or ameliorating neurodegenerative or neurological disorders or neuronal injuries in a subject in need thereof. The method includes administering an effective amount of CiNs to the subject, preferably at the site in need of treatment.

BRIEF DESCRIPTION OF THE DRAWINGS

FIG. 3A shows whole-cell current-clamp recording of CiNs and action potentials elicited by current injection. FIG. 3B shows whole-cell voltage-clamp recording of CiNs and inward and outward currents. FIGS. 3C and D show the functional membrane properties of the CiNs after co-culture with primary astrocytes. FIG. 3E shows recording of evoked EPSCs from CiNs co-cultured with primary astrocytes.

FIGS. 6A and 6B show the activation of master neuronal genes (FIG. 6A) and the suppression of fibroblast genes (FIG. 6B) as validated by real-time qPCR. FIGS. 6C and 6D show the effect of individual chemicals on the expression of Ngn2 and fibroblast genes at 48 h. FIGS. 6E and 6F show the effect of individual chemicals on global gene expression. "Up-regulated" represents genes with expression levels up-regulated by more than 2-fold compared to fibroblasts, while "down-regulated" represents genes with expression level down regulated by more than 2-fold compared to fibroblasts. FIG. 6G is a bar graph showing the effect of small molecule treatment on neuron-specific genes. NI, not induced; The data are presented as the mean+/−SEM.

DETAILED DESCRIPTION OF THE INVENTION

Figure 1A:
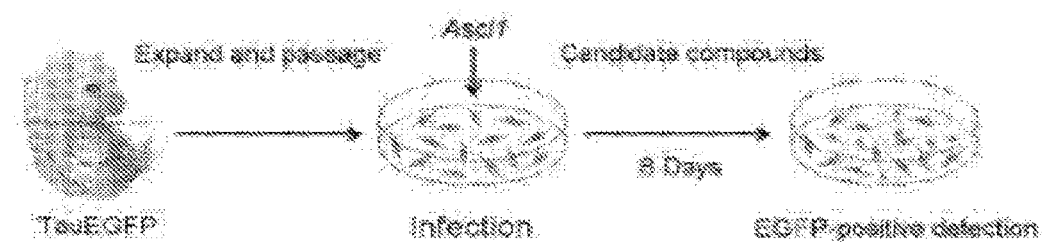
FIG. 1A is a schematic showing small-molecule (SM) screening for candidate compounds.

A novel cocktail of small molecules capable of establishing neuronal features in non-neuronal cells, efficiently and directly, is disclosed. When included in a fibroblast culture medium, the small molecules activate the endogenous expression of neuronal-specific genes, down-regulate fibroblasts-specific program in the early stage of reprogramming, and finally, convert fibroblasts to functional neurons.

An alternative strategy based on the use of small molecules to induce cell-lineage reprogramming as disclosed herein is advantageous because such a strategy would be non-immunogenic, cost-effective and easy to manipulate and standardize. In addition, the manipulation of small molecules is reversible and cells are permeable to small molecules. Ding, et al., *Biotechnol.*, 22:833-840 (2004)). This strategy can be translated into therapeutic applications (Yu et al., *Curr Opin Genet Dev.*, 28:50-56 (2014)).

I. Definitions

"Agonist," or "activator," "upregulator," as used herein refers to a substance capable of detectably increasing the expression or activity of a given gene or activity. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or more, higher than the expression or activity in the absence of the agonist.

"Chemically induced neurons" (CiNs) as used herein refers to neuron-like cells derived from a cell that is not a neuron (i.e., a non-neuronal cell), by contacting the non-neuronal cell with chemical compounds.

"CINPs" as used herein refer to chemical compounds that induce/confer neuron-like properties in/to non-neuronal cells.

"Culture" means a population of cells grown in a cell culture medium and optionally passaged. A cell culture may be a primary culture (e.g., a culture that has not been passaged) or may be a secondary or subsequent culture (e.g., a population of cells which have been subcultured or passaged one or more times).

"Exogenous" refers to a molecule or substance (e.g., nucleic acid or protein) that originates from outside a given cell or organism. Conversely, the term "endogenous" refers to a molecule or substance that is native to, or originates within, a given cell or organism.

"Expression" or "expressed" as used herein in reference to a gene means the transcriptional and/or translational product of that gene.

"Glycogen synthase kinase (GSK) inhibitor" as used herein refers to an agent that inhibits a GSK. GSK include GSK 1, GSK 2 and GSK 3.

"Induction medium" as used herein refers to cell culture medium which additionally includes CINPs in effective amounts to induce/confer neuron-like properties in/to non-neuronal cells.

"Inhibitor" as used herein refers to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

"Isolated" or "purified" when referring to CiNs means chemically induced neurons at least 30%, 35%, 40%, 45%, 50%, 55%, 60%, 65%, 70%, 75%, 80%, 85%, 90%, 95%, or 99% free of contaminating cell types such as non-neuronal cells. The isolated CiNs may also be substantially free of soluble, naturally occurring molecules.

"Maturation medium" as used herein refers to induction medium plus Forskolin 10 µM, BDNF 20 ng/ml and GDNF 20 ng/ml.

"Media" and "culture medium" as used herein refers to the cell culture milieu. Media is typically an isotonic solution, and can be liquid, gelatinous, or semi-solid, for example, to provide a matrix for cell adhesion or support. Media, as used herein, can include the components for nutritional, chemical, and structural support necessary for culturing a cell.

"Nucleic acid" as used herein refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA as well as single and double stranded RNA (including miRNA).

"Neuron-like" when used to refer to a reprogrammed cell refers to the cell possessing properties normally attributed to neurons/nerve cells i.e., "neuron-like properties" such as morphology (for example neurite outgrowth), expression of neuronal-specific markers such as MAP2, NF-H, mature neuronal markers such as NeuN, excitatory or inhibitory membrane properties as evidenced by expression of vGlut and/or Gad67, and membrane depolarization as measured in a patch-clamp assay.

"Neurogenic nucleic acids" as used herein refer to nucleic acids whose introduction into a non-neuronal cell induces conversion of non-neuronal cells into neuron-like cells or confers onto the non-neuronal cell, neuron-like properties.

"Neuronal-like morphology" is used herein interchangeably with "neuron-morphology" to refer to morphology characteristic of neurons, such as the presence of a soma/cell body, dendrites, axon and/or synapses.

"Non-neuronal cells" as used herein refers to cells which are not characterized as neurons based on a combination of morphology and functions associated with neurons.

"Reprogramming" as used herein refers to the conversion of a one specific cell type to another. For example, a cell that is not a neuron can be reprogrammed into a cell with neuron-like cells. Where the cell is reprogrammed into a neuron-like cell using chemical compounds, the resulting cell is a chemically induced neuron-like cell.

"Transforming growth factor beta (TGFβ) receptor inhibitor" as used herein refers to an agent that inhibits the TGFβ receptor. TGFβ receptors are single pass serine/threonine kinase receptors. Three TGF-β receptor types include receptor types I, II and III, i.e., TGF-β receptor 1, TGF-β receptor 2 and TGF-β receptor 3.

"Treating", and/or "ameliorating" neurodegenerative or neurological disorders or neuronal injuries as used herein refer to reducing/decreasing the symptoms associated with the neurodegenerative or neurological disorders or neuronal injury.

II. Compositions

A number of studies have employed small molecules to enhance the efficiency of direct reprogramming or replace part of the reprogramming transcription factors (Ladewig et al., *Nat Methods*, 9:575-578 (2012); Liu et al., *Nat Commun.*, 4:2183 (2013); Xu et al., *Cell Stem Cell*, 16:119-134 (2015)). However, the feasibility of a pure small-molecule approach for direct cell fate reprogramming without genetic manipulation has not been demonstrated. The compositions disclosed herein include a cocktail of small molecules that induce the conversion of non-neuronal cells into cells with neuron-like properties, independent of recombinant neurogenic nucleic acids.

A. Small Molecules Inducing Neuronal Cell Properties

Small molecules have been identified, which can be used to reprogram partially or completely differentiated cells into a neuron-like cell. Chemical compounds that induce/confer neuron-like properties (i.e., CINPs) in non-neuronal cells include small molecules having a molecular weight of less than 2,000 Daltons, more preferably less than 1,500 Daltons, and most preferably less than 1,000 Dalton. The small molecules can have a molecular weight less than or equal to 900 Daltons, or, less than or equal to 500 Daltons. Larger molecules can be used in chemically-induced reprogramming, preferably targeting the same pathway as the small molecules disclosed herein.

The data disclosed herein shows that activation of the neural-fate-determining genes/factors and the down-regulation of fibroblast-fate-determining factors (for example) were induced within 24 hours following culture in CINPs. Additionally, following a 48 hour-chemical induction, the expression of NeuroD1 and Ngn2, two neural-fate mastering genes, was dramatically induced. Accordingly, the cocktail of CINPs can be used to up-regulate neural-fate-determining genes in a cell that is not a neuronal cell, by culturing the cell in the presence of CINPs for at least 24 hours, preferably, between 24 and 48 hours. In some embodiments the cells are cultured in CINPs for 3-24 days, for example, 3, 4, 5, 6, 7, 8, 9, 10, 11, 12, or 13 days. In the most preferred embodiment, upregulation of neural-fate-determining genes/factors and down regulation of the non-neuronal cell fate determining genes results in CiNs, determined morphologically and functionally, as disclosed herein.

CINPs include: (1) a cyclic AMP agonist, (2) a neurogenic small molecule (3) a glycogen synthase kinase (GSK) inhibitor, (4) a transforming growth factor β inhibitor, (5) a BET family bromodomain inhibitor, and combinations thereof. Exemplary CINPs and useful concentrations are shown in Table 1. Further, it is within the abilities of one of ordinary skill in the art to select concentrations of other agents disclosed herein based on the effective amounts disclosed for specific compounds.

(i) Cyclic AMP Agonists

A preferred cAMP agonist is forskolin ("F"). However, any cAMP agonist can be included in the cocktail of CINPs disclosed herein. Examples include, but are not limited to prostaglandin E2 (PGE2), rolipram (for example, in a concentration of 50 μM), genistein and cAMP analogs such as DBcAMP (for example, in a concentration of 10 μM) or 8-bromo-cAMP (for example, in a concentration of 200 μM. The cocktail of CINPs include a cyclic AMP agonist, for example, forskolin in a concentration range from 5 to 500 μM, preferably between 20 to 300 and even more preferably, between 20 and 200 μM and most preferably, between 50 and 100 μM. For example, the CINP composition can include forskolin concentrations of 20, 40, 60, 80, 100, 120, 140, 160, 180, or 200 μM. Concentrations that fall between these numbers are contemplated as one of ordinary skill in the art can readily fine tune the effective amounts needed.

(ii) Neurogenic Small Molecules

The compositions in some embodiments include one or more neurogenic small molecules. A preferred compound is ISX 9 ("I"). ISX9 can be included in a concentration range from 5 to 100 μM, preferably between 10 and 40 and even more preferably, between 10 and 40 μM and most preferably between 10 and 20 μM. For example, the cocktail of CINPs can include ISX 9 concentrations of 5, 10, 15, 20, 25, 30, 35, 40, 45, or 50 μM. Concentrations that fall between these numbers are contemplated as one of ordinary skill in the art can readily fine tune the effective amounts needed.

(iii) GSK Inhibitor

The GSK inhibitor preferably inhibits GSK3 and preferably, is selective for GSK3. A suitable GSK inhibitor is the aminopyrimidine, CHIR99021 ("C"), which is the glycogen synthase kinase 3 inhibitor. The CINP compositions include CHIR99021 in a concentration range from 2 to 100 μM, preferably between 5 and 50, and even more preferably, between 10 and 20 μM. Most preferably, the concentration is between 2 and 10 μM. For example, the CINP can include CHIR99021 in concentrations of 2, 5, 10, 15, 20, 25, 30, 35, 40, 45, or 50 μM. Concentrations that fall between these numbers are contemplated, as one of ordinary skill in the art can readily fine tune the effective amounts needed.

However, other GSK inhibitors are commercially available and are contemplated. Examples include, but are not limited to BIO-acetoxime (for example 1 μM); GSK 3I inhibitor XV (For example 0.4 μM); SB-216763 (for example, 10 μM); CHIR 99021 trihydrochloride, which is the hydrochloride salt of CHIR99021; GSK-3 Inhibitor IX [((2Z, 3E)-6'-bromo-3-(hydroxyimino)-[2,3'-biindolinylidene]-2'-one]; GSK 3 IX [6-Bromoindirubin-3'-oxime]; GSK-3β Inhibitor XII [3-[[6-(3-Aminophenyl)-7H-pyrrolo[2,3-d]pyrimidin-4-yl]oxy]phenol]; GSK-3 Inhibitor XVI [6-(2-(4-(2,4-dichlorophenyl)-5-(4-methyl-1H-imidazol-2-yl)-pyrimidin-2-ylamino)ethyl-amino)-nicotinonitrile]; SB-415286 [3-[(3-chloro-4-hydroxyphenyl)amino]-4-(2-nitrophenyl)-1H-pyrrole-2,5-dione]; and Bio [(2'Z,3'E)-6-bromoindirubin-3'-oxime].

(iv) Transforming Growth Factor β Inhibitor

The TGFβ inhibitor is preferably inhibits the TGFβ type 1 receptor activing receptor-like kinase (ALK) 5 in some embodiments, and can additionally inhibit ALK 4 and the nodal type receptor 1 receptor ALK7 in other embodiments Preferably, the TGFβ inhibitor has no effect on BMP signaling. A preferred TGFβ inhibitor is SB431542 ("S") (Inman, et al., *Mol. Pharmacol.*, 62(1):65-74 (2002)). SB431542 is included in the CINP compositions in a concentration range from 1 to 50 μM, preferably between 2 and 40 and even more preferably, between 2 and 10 μM.

Other TGFβ inhibitors are known in the art and are commercially available. Examples include E-616452 [2-(3-(6-Methylpyridin-2-yl)-1H-pyrazol-4-yl)-1,5-naphthyridine]; A 83-01 [3-(6-Methyl-2-pyridinyl)-N-phenyl-4-(4-quinolinyl)-1H-pyrazole-1-carbothioamide]; SB 505124 [2-[4-(1,3-Benzodioxol-5-yl)-2-(1,1-dimethylethyl)-1H-imidazol-5-yl]-6-methyl-pyridine]; GW 788388 [4-[4-[3-(2-Pyridinyl)-1H-pyrazol-4-yl]-2-pyridinyl]-N-(tetrahydro-2H-pyran-4-yl)-benzamide]; and SB 525334 [6-[2-(1,1-Dimethylethyl)-5-(6-methyl-2-pyridinyl)-1H-imidazol-4-yl]quinoxaline], and dorsomorphin.

(v) A BET Family Bromodomain Inhibitor

The compositions disclosed herein include a BET family bromodomain inhibitor in some embodiments. A preferred BET family bromodomain inhibitor is I-BET151 ("B") or I-BET 151 hydrochloride. I-BET151 is included in the CINP compositions in a concentration range from 2 to 100 μM, preferably between 5 and 50 and even more preferably, between 5 and 20 μM. For example, the CINP can include a BET family bromodomain inhibitor as disclosed herein in concentrations of 2, 5, 10, 15, 20, 25, 30, 35, 40, 45, or 50 μM. Concentrations that fall between these numbers are contemplated, as one of ordinary skill in the art can readily fine tune the effective amounts needed.

Other suitable BET family bromodomain inhibitors are known in the art and are commercially available. Examples include, but are not limited to PFI 1 [2-methoxy-N-(3-methyl-2-oxo-1,2,3,4-tetrahydroquinazolin-6-yl)benzenesulfonamide] (for example, 5 μM); JQ1 (for example, 1 μM); bromosporine (for example, 1 μM); and ICBP 112 [1-[7-(3,4-dimethoxyphenyl)-9-[[(3S)-1-methylpiperidin-3-yl]methoxy]-2,3,4,5-tetrahydro-1,4-benzoxazepin-4-yl]propan-1-one] (for example, 10 μM).

The agents disclosed herein are preferably used in combination i.e., a cocktail. In one embodiment, the cocktail of CINPs includes a combination of FICS. In another embodiment, the cocktail of CINPs includes a combination of FICB. In other embodiments, the cocktail of CINPs include FICSB.

B. Cells to be Induced

The CiNs are obtained by inducing partially or completely differentiated cells obtained from any mammal (e.g., bovine, ovine, porcine, canine, feline, equine, primate), preferably a human. Sources include bone marrow, fibroblasts, fetal tissue (e.g., fetal liver tissue), peripheral blood, umbilical cord blood, pancreas, skin or any organ or tissue. In a preferred embodiment, the CiNs are obtained from chemically induced fibroblasts, adipose-derived stem cells, non-neuronal cells from the central nervous system or cells from the intestinal epithelium. In a more preferred embodiment, CiNs are obtained from chemically induced neonatal (for example foreskin) or adult fibroblasts. However, CiNs can be obtained from other cell types including, but not limited to: multipotent stem cells, cells of hematological origin, cells of embryonic origin, skin derived cells, adipose cells, epithelial cells, endothelial cells, mesenchymal cells, parenchymal cells, neurological cells, for example, astrocytes and glial cells, and connective tissue cells.

The cell to be reprogrammed can be obtained from a sample obtained from a mammalian subject. The subject can be any mammal (e.g., bovine, ovine, porcine, canine, feline, equine, primate), including a human. A sample of cells may be obtained from any of a number of different sources including, for example, bone marrow, fetal tissue (e.g., fetal liver tissue), peripheral blood, umbilical cord blood, pancreas, skin or any organ or tissue.

Cells may be isolated by disaggregating an appropriate organ or tissue which is to serve as the cell source using techniques known to those skilled in the art. For example, the tissue or organ can be disaggregated mechanically and/or treated with digestive enzymes and/or chelating agents that weaken the connections between neighboring cells, so that the tissue can be dispersed to form a suspension of individual cells without appreciable cell breakage. Enzymatic dissociation can be accomplished by mincing the tissue and treating the minced tissue with one or more enzymes such as trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators.

C. Chemically Induced Neurons (CiNs)

CiNs disclosed herein are neuron-like, morphologically and functionally i.e., CiNs possess properties traditionally attributed to neurons. However, these cells are different from naturally occurring neurons and/or from the naturally occurring cells from which they are obtained, because their gene expression profile (which results from the CINPs treatment) is different from that seen in naturally occurring neurons or the cells from which they are obtained. In a preferred embodiment, CiNs exhibit a combination of morphological and functional characteristics attributed to neurons and down regulation of at least one gene attributed to the cell from which it is obtained. Genes that are useful as markers of cells from different lineages are known in the art.

CiNs are characterized neuron-like based on a morphology characteristic of neurons, for example neurite outgrowth. Neuronal-like morphology can be determined using well established methods, for example, microscopy, reviewed for example in Parekh, et al., *Neuron*, 77(6):1017-1038 (2013). Methods for quantifying neuronal morphology are described for example in Ho, et al., *BMC Bioinformatics*, 12:230 (2011).

In addition, CiNs express one or more neuron specific markers such as TUJ1 (Neuron-specific class III beta-tubulin), MAP2, NF-H and NeuN. MAP-2 is a neuron-specific cytoskeletal protein that is used as a marker of neuronal phenotype. Izant, et al., *Proc Natl Acad Sci USA.*, 77:4741-5 (1980). NeuN is a neuronal specific nuclear protein identified by Mullen, et al., *Development*, 116:201-11 (1992). This protein, which they called Neuronal Nuclei (NeuN), was detected in most neuronal cell types throughout the central and peripheral nervous systems of adult mice. Additional markers that may be used to identify CiNs are reviewed for example in *Mater Methods*, 3:196 (2013). CiNs show upregulation of neuron-specific genes. For example the genes can be upregulated by 2 fold, 3 fold, 4 fold 5 fold or 6 fold. However, upregulation included increased levels of expression of a gene considered a neuron-specific genes, when compared to the levels in the cell/cell type from which the CiNs was obtained.

Further, CiNs can have similar membrane properties exhibited by neurons; these membrane properties are absent in the cells from which they are obtained. For example, excitatory or inhibitory membrane properties are evidenced by expression of neurotransmitter transporters such as vesicular glutamate transporter (vGlut) and/or Gad67 (glutamate decarboxylase 67), and membrane depolarization as measured in a patch-clamp assay. Glutamatergic neurons express at least one of three known vesicular glutamate transporters, VGLUT1, VGLUT2, or VGLUT3. These transporters mediate glutamate uptake into synaptic vesicles and are driven by a proton electrochemical gradient. The expression level of VGLUTs has been shown to determine the amount of glutamate loaded into vesicles and released, thereby regulating the efficacy of neurotransmission. Wojcik, et al., *PNAS*, 101(18:7158-7163 (2004). The inhibitory neurotransmitter γ-amino butyric acid (GABA) is synthesized by two isoforms of the enzyme glutamic acid decarboxylase (GAD): GAD65 and GAD67. In primary neurons, GAD67 is targeted to Golgi membranes, cytosolic vesicles, and presynaptic clusters independent of GAD65. Kanaani, et al., J. Cell. Biol., 190(5):911-925). In addition, the CiNs show downregulation of genes characteristic of the lineage from which they are obtained. For example, when obtained from fibroblasts, fibroblast hallmark genes such as Fap, Des, Slug, Dcn, FSp1, Collagen 1 and Twist2 are down-regulated in CiNs. Markers used to identify specific cell types are known in the art. For example, hepatocyte cell markers include, but are not limited to albumin, Cytochrome P450 (Cyp)3A4, CYPB6, CYP1A2, CYP2C9, and/or CYP2C19; adipocyte markers include for example, adiponectin, fatty acid binding protein P4, and leptin. The CiNs show downregulation of one or more genes known in the art as a marker of the cell type from which it is obtained. The gene can be downregulated by 2 fold, 3 fold, 4 fold, 5, fold, etc., or completely silenced The CiNs in some embodiments additionally include nucleic acids that induce conversion of non-neuronal cells into neuron-like cells ("neurogenic nucleic acid"), introduced into the cell using genetic engineering techniques. Examples of neurogenic transcription factors and nucleotides include Ascl1, Zic1, Olig2, Brn2/4, NeuroD1 and Myt1 (Vierbuchen, et al., Nature, 463:1035-1041 (2010)); microRNAs (miRNAs) miR-9/9 or miR-124 (miR-9/9*-124) (Yoo, et al., Nature, 476(7359):228-31 (2011) and Ambasudhan, et al., Cell Stem Cell, 9(2):113-118 (2001); neurogenin 2 (NGN2); SOX11.

In a more preferred embodiment, the CiNs do not additionally contain neurogenic nucleic acid introduced into the cell using genetic engineering techniques. In this embodiment, the CiNs is generated from a process that only includes exposing donor cells to a cocktail of small molecules as disclosed herein.

D. CiNs-Based Therapeutic Compositions

CiNs can be formulated for administration, delivery or contacting a subject, tissue or cell using a suitable pharmaceutically acceptable carrier. In some embodiments, the cells are simply suspended in a physiological buffer. In other embodiments, the cells are provided with, or incorporated into a support structure. One strategy includes encapsulating/suspending CiNs in a suitable polymeric support. The support structures may be biodegradable or non-biodegradable, in whole or in part. The support may be formed of a natural or synthetic polymer. Natural polymers include collagen, hyaluronic acid, polysaccharides, alginates and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters. These may be in for the form of implants, tubes, meshes, or hydrogels. The support structure may be a loose woven or non-woven mesh, where the cells are seeded in and onto the mesh. The structure may include solid structural supports. The support may be a tube, for example, a neural tube for regrowth of neural axons.

For example, the cells can be suspended in a hydrogel matrix of collagen, alginate or Matrigel®. Common non-biodegradable cell-carriers in neural tissue engineering include silicone, polyvinyl alcohol (PVA) and copolymer poly(acrylonitrile-co-vinyl chloride) (P(AN/VC)), polysulphone (PSU) and poly(ethersulphone) (PES), poly(ethylene terephthalate) (PET) and polypropylene (PP). Reviewed in Wong, et al., Int. J. Mol Sci. 15:10669-10723 (2014). See also, Blurton-Jones, et al., Proc. Natl. Acad. Sci., 106 (32):13594-9 (2009); Jin, et al, J. Cereb. Blood Flow Metab., 30:534-44 (2009); and Lundberg, et al, Neuroradiology, 51:661-7 (2009). Transplantation of microencapsulated cells is known in the art, and is disclosed for example in Balladur et al., Surgery, 117:189-94 (1995); and Dixit et al., Cell Transplantation, 1:275-79 (1992).

The CiNs-based therapeutic compositions include effective amounts of CiNs cells for use in the methods disclosed herein. For example, a dose of $10^4$ $10^5$ cells can be initially administered, and the subject monitored for an effect (e.g., engraftment of the cells, improved neural function, increased neuronal density in an affected area). The dose CiNs can be in the range of $10^3$-$10^7$, $10^4$-$10^7$, $10^5$-$10^8$, $10^6$-$10^9$, or $10^6$-$10^8$ cells. The pharmaceutical preparation including CiNs can be packaged or prepared in unit dosage form. The cells can be lyophilized and/or frozen for increased shelf life, and resuspended prior to administration. In such form, the cellular preparation is subdivided into unit doses containing appropriate quantities of the active component, e.g., according to the dose of the therapeutic agent. The unit dosage form can be a packaged preparation, the package containing discrete quantities of preparation. The composition can, if desired, also contain other compatible therapeutic agents.

III. Methods of Making

A. Preparation Before Chemical Induction

The cell culture surface/device is prepared for cell culture, using methods known in the art. Using cells cultured on Matrigel as an example, Matrigel (growth factors reduced; BD Biosciences) is thawed on ice according to the manufacturer's instruction and dilute it in pre-cold PBS with a ratio of 1:30. Diluted matrigel is be added to 6-well plates. The quantity used should be to be sufficient to cover the entire growth surface of the plates. The plates (plus matrigel) are kept at 37° C. for 30 minutes to be ready to use. Passage 1-2 of cells to be induced, for example MEFs, are dissociated using 0.25% trypsin and seeded them into the matrigel-coated plates at a preferred density of 100,000 cells per well and cultured in fibroblast medium. Cells are grown in the fibroblast medium for until confluent (for example, for 3-5 days, preferably, 4-5 days). In a preferred embodiment, the cells to be induced are not chemically induced until confluent.)

B. Induction of CiNs

CiNs are induced by providing partially or completely differentiated cells in a culture media containing the CINPs for a sufficient period of time to result in reprogramming the cells into CiNs. The reprogrammed cells are characterized as CiNs based on morphology, expression of neuronal markers such as MAP2, NF-H, NeuN, vGlut and/or Gad67, and/or functional membrane depolarization, as measured in a patch-clamp assay for example.

When MEFs are grown to confluence, the culture medium is changed to neuronal induction medium which contains Neurobasal Media, 1% N2 and 2% B27 supplements, 1% GlutaMAX, 1% penicillin-streptomycin and bFGF (100-250 ng/ml). These agents are commercially available.

The small molecules are dissolved and diluted in DMSO according to the manufacturer's instruction. The small molecules are added to the neuronal induction media in advance.

i. Chemical Induction

In one embodiment, the cell to be reprogrammed is contacted with a combination of FICS. In another embodiment, the cell to be reprogrammed is contacted with a combination of FICB. In still other embodiments, the cell to be reprogrammed is contacted with FICSB.

The cells to be induced are contacted with a cocktail of CINPs, which includes CINPs in an amount effective to induce and/or enhance reprogramming of non-nerve cells into CiNs. One of ordinary skill in the art can readily determine the concentrations of the CINPs disclosed herein, required to provide complete reprogramming using methods outlined in the examples below, or other methods known in the art. Exemplary small molecule concentrations and concentrations are as follows: ISX9 ("I"), 20 µM; Forskolin ("F"), 100 LVM; CHIR99021 ("C"), 20 µM; and I-BET151 ("B"), 0.5-2 µM.

Figure 2A:
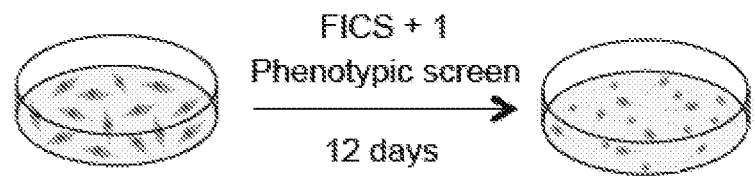
FIG. 2A is a diagram of the process to identify small molecule candidates that facilitate reprogramming.
Figure 2B:
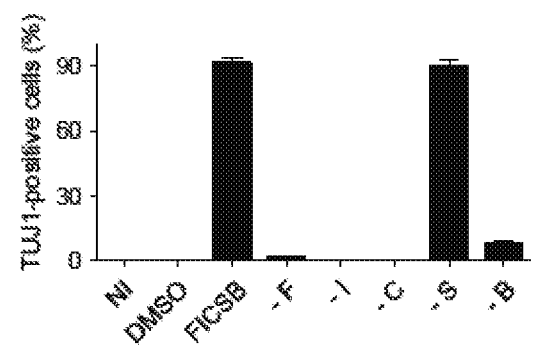
FIGS. 2B-2D shows quantification of TUJ1-positive cells (FIG. 2B), NeuN/TUJ1-double positive cells (FIG. 2C) and TAUEGFP/TUJ1-double positive cells (FIG. 2D) induced by FICSB and the effect of withdrawing individual chemicals from FICSB.
Figure 2C:
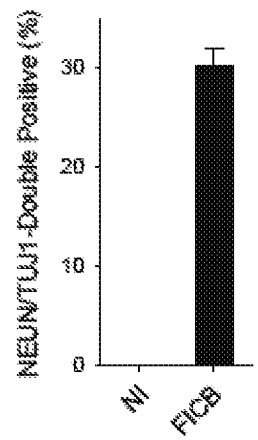
Figure 2D:
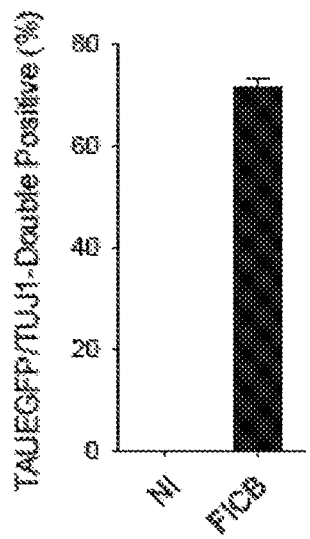
Figure 2E:
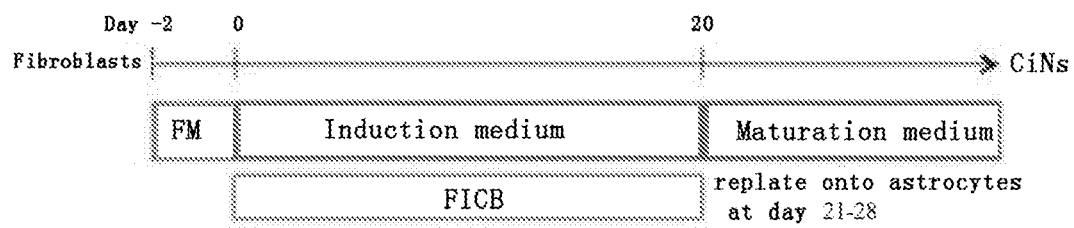
FIG. 2E is a schematic showing generation of CiNs.
Figure 2F:
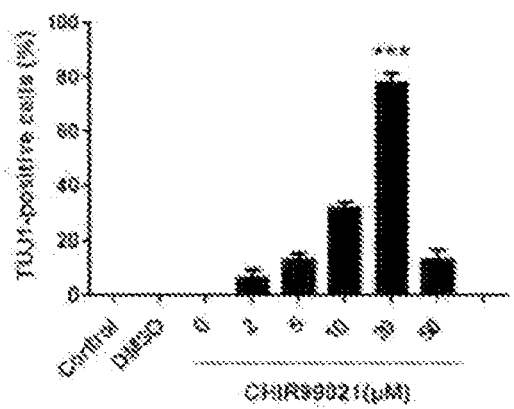
FIGS. 2F-I show the dose dependent effect of four small molecules on the generation of neurons. The efficiency of neuron generation (based on TUJ1 positivity) was determined using ten random fields for each condition. Control, not induced; DMSO, vehicle control.
Figure 2G:
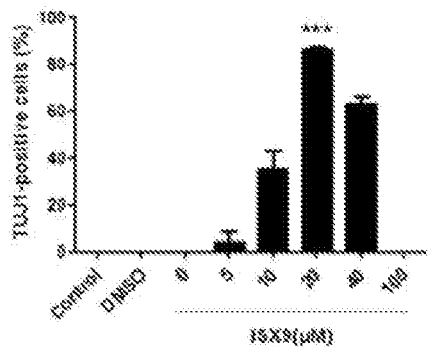
Figure 2H:
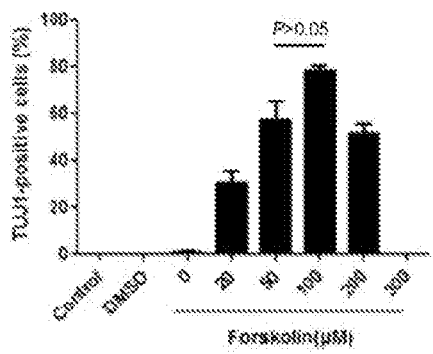
Figure 2I:
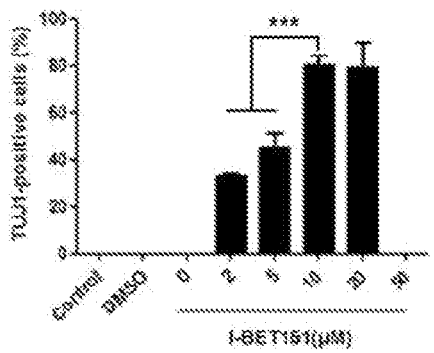

A schematic for the generation of CiNs using the CINPs is shown for example in FIG. 2E. Cells to be reprogrammed are cultured in normal cell culture medium suitable for that cell type for a period of one to two days, preferably, 2 days. The cells are then transferred into an induction medium for a time period between 14 and 24 days. For example, the cells can be cultured in induction medium for 14, 15, 16, 17, 18, 19, 20, 21, 22, 23, or 24 days. In the case of fibroblasts for example, the cells are preferably grown/cultured in induction medium for about 20 days. It is within the ability of one of ordinary skill in the art to vary the length of time in culture effective to result in CiNs based on evaluation of the presence of characteristics attributed to neurons which are known, and disclosed herein. Culture medium (neuronal induction medium plus the small molecules) is refreshed every 3-4 days during the chemical induction period. It is preferable to prepare the culture medium containing the small molecules freshly before inducing.

In some embodiments, the cocktail of CINPs can be used to up-regulate neural-fate-determining genes in a cell that is not a neuronal cell, by culturing the cell in the presence of CINPs for at least 24 hours, preferably, between 24 and 48 hours. For example, the cells are cultured in CINPs for 3-24 days, for example, 3, 4, 5, 6, 7, 8, 9, 10, 11, 12, or 13 days. In the most preferred embodiment however, upregulation of neural-fate-determining genes/factors and down regulation of the non-neuronal cell fate determining genes results in CiNs, determined morphologically and functionally, as disclosed herein.

The cyclic AMP agonist, for example, forskolin is administered in a concentration range from 5 to 500 μM, preferably between 20 to 300 μM and even more preferably, between 20 and 200 μM. The neurogenic small molecule, for example, ISX9, is administered in a concentration range from 5 to 200 μM, preferably between 10 and 100 and even more preferably, between 10 and 50 μM. In embodiments employing a BET family bromodomain inhibitor for example, I-BET151, the method further includes treating the cells with an additional small molecule may be added to promote cell survival and reprogramming. Exemplary small molecules include an inhibitor of the Rho-associated coiled-coil forming protein serine/threonine kinase (ROCK) family or a p38 MAPK inhibitor. In these embodiments, the additional small molecule in added in a concentration between 0.5 to 5 μM, at the early stage of induction, in some embodiments between day 0-4, in other embodiments between day 0-8. Exemplary ROCK inhibitors for this purpose isY27632 [(+)-(R)-trans-4-(1-aminoethyl)-N-(4-pyridyl)cyclohexanecarboxamide dihydrochloride or a related compound, Y-30141 [(+)-(R)-trans-4-(1-aminoethyl)-N-(1H-pyrrolo[2, 3-b]pyridin-4-yl)cyclohexanecarboxamide dihydrochloride] (Ishizaki, et al., *Mol. Pharmacol.*, 57(5):976-83 (2000), or fasudil, added at a preferred concentration of 2 μM. Exemplary p38 inhibitors include BIRB796 (doramapimod) and SB203580 (available for example from Cell Signaling Technology, #5633), added at a preferred concentration of 1 μM.

Different cell types can have different optimal concentrations of small molecules. These concentrations can be determined by routine experimentation based on the studies described herein.

ii. Maturation

Following culture in induction medium, the cells are cultured in a maturation medium for at least 10 days, preferably, for a period greater than 10 days. For example, the cells can be cultured in maturation medium for 10, 11, 12, 13, 14, 15, 16, 17, 18, 19, 20, 21, 22, 23, 24, 25, 26, 27, 28, 29 or 30 days with a cell culture medium (maturation) change preferably every 2-3 days, following which, cells of a second type (i.e., CiNs) are obtained. In a preferred embodiment, the cells are cultured in maturation medium for a period between 14 and 21 days. In this step, cells are preferably replated in maturation medium, in combination with primary astrocytes, following which CiNs are obtained. In this embodiment, mouse primary postnatal cortical neurons or astrocytes are isolated and cultured for about one week before re-plating the induced cells, as exemplified herein (See the Examples). The induced cells are dissociated for example, by using 0.25% trypsin or mechanistically detached from the cell culture plate using a pipette. The cells are preferably centrifuged (for example, for 3 min at 1000 rpm at room temperature, the supernatant discarded, fresh maturation medium (the neuronal induction medium plus bFGF 50 ng/ml, Forskolin 10 μM, BDNF 20 ng/ml and GDNF 20 ng/ml) added to gently re-suspend the cells and re-plate them to co-culture with pre-existing primary astrocytes/primary neurons. Alternatively, the cells can be sequentially switched to co-culture with astrocytes. For example, neuronal induction medium can be switched to maturation medium to further promote the extent of reprogramming and maturation. Cells are cultured in maturation medium for a time period ranging from 5-8 days, following which the cells are dissociated and co-cultured with primary astrocytes/pre-existing primary neurons as disclosed herein The exemplary time periods provided herein are not limiting. It is within the ability of one of ordinary skill in the art to vary the length of time in culture effective to result in CiNs based on evaluation of the presence of characteristics attributed to neurons which are known, and disclosed herein.

The disclosed methods yield CiNs without the need to transfect cells with neurogenic nucleic acids.

C. Isolation of CiNs

A purified population of CiNs can be obtained, for example, by extraction (e.g., via density gradient centrifugation and/or flow cytometry) from a culture source. Purity can be measured by any appropriate method. The CiNs cells can be 99%-100% purified, for example, by flow cytometry (e.g., FACS analysis). CiNs can be isolated by, for example, utilizing molecules (e.g., antibodies, antibody derivatives, ligands or Fc-peptide fusion molecules) that bind to a marker (e.g., TUJ1, MAP2, NF-H and NeuN or a combination of markers) on the CiNs, and thereby positively selecting cells that bind the molecule (i.e., a positive selection). Isolation of neurons using a NeuN antibody using FACS is described for example in Guez-Barber, *J. Neurosci. Methods.*, 203(1):10-18 (2012).

Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of CiNs can be obtained.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Isolation of living neurons using immunomagnetic sorting is described for example in Konishi, et al. *Am. J. Pathol.*, 161(5):1567-1576 (2002). Antibodies may be conjugated with markers, such as magnetic beads, which allow for direct separation, biotin, which can be removed with avidin or streptavidin bound to a support, or fluorochromes, which can be used with a fluorescence activated cell sorter, to allow for ease of separation of the particular cell type. Any technique may be employed which is not unduly detrimental to the viability of the CiNs. In one embodiment, the cells are incubated with an antibody against a marker (e.g., a TUJ1, MAP2, NF-H or NeuN antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest, the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, and Texas red.

D. Culture and Preservation of CiNs

The CiNs can be expanded in culture and stored for later retrieval and use. Once a culture of cells is established, the population of cells is mitotically expanded in vitro by passage to fresh medium as cell density dictates, under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor). Cultured cells can be transferred to fresh medium when sufficient cell density is reached. Cell culture medium for maintaining neuronal cells are commercially available.

Cells can be cryopreserved for storage according to known methods, such as those described in Doyle, et al., (eds.), 1995, Cell & Tissue Culture: Laboratory Procedures, John Wiley & Sons, Chichester. For example, cells may be suspended in a "freeze medium" such as culture medium containing 15-20% fetal bovine serum (FBS) and 10% dimethylsulfoxide (DMSO), with or without 5-10% glycerol, at a density, for example, of about $4\text{-}10 \times 10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

IV. Methods of Use

The approach of direct reprogramming has been used in disease modeling, suggesting promising applications in regenerative medicine (Xu, et al., *Cell Stem Cell*, 16:119-134 (2015)). The in vivo direct reprogramming of cell fates may suggest a promising future to regenerate in situ for treating diseases (Xu et al., *Cell Stem Cell*, 16:119-134 (2015)). Cell-based therapy is seeing application in human clinical trials. For example, Geron Corporation and SanBio, Inc. have carried out clinical trials for human embryonic stem cell-based and bone marrow derived cells, respectively, in neuronal disorders.

The CiNs are useful in methods for treating and/or ameliorating neurodegenerative or neurological disorders or neuronal injuries in a subject in need thereof (individuals having a neuronal cell deficiency). In a preferred embodiment, the CiNs are obtained from autologous cells, i.e., the donor cells are autologous. However, the cells can be obtained from heterologous cells. In one embodiment, the donor cells are obtained from a donor genetically related to the recipient. In another embodiment, donor cells are obtained from a donor genetically un-related to the recipient. If the human CiNs are derived from a heterologous (non-autologous/allogenic) source compared to the recipient subject, concomitant immunosuppression therapy is typically administered, e.g., administration of the immunosuppressive agent cyclosporine or FK506.

The method includes administering to the individual/subject an effective amount of CiNs, thereby treating and/or ameliorating symptoms associated with the neurodegenerative disorder or neuronal injury. In some embodiments, the CiNs are administered to the site of the neurodegeneration or neuronal injury in the individual for example, by injection into the lesion site using a syringe positioning device. CiNs can be transplanted directly into parenchymal or intrathecal sites of the central nervous system, according to the disease being treated (U.S. Pat. No. 5,968,829 for example). CiNs can be administered to a subject in need thereof, using known methods of administering cells to neuronal tissues such as the brain or spinal as described for example in Blurton-Jones, et al., *Proc. Natl. Acad. Sci.*, 106 (32): 13594-9 (2009); Jin, et al, *J. Cereb. Blood Flow Metab.*, 30:534-44 (2009); and Lundberg, et al, *Neuroradiology*, 51:661-7 (2009).

As with any therapy, the course of treatment is best determined on an individual basis depending on the particular characteristics of the subject and the type of treatment selected. The treatment can be administered to the subject one time, on a periodic basis (e.g., bi-weekly, monthly) or any applicable basis that is therapeutically effective. The treatment can be administered alone or in combination with another therapeutic agent, e.g., an agent that reduces pain, or an agent that encourages neuronal function or growth. The additional therapeutic agent can be administered simultaneously with the CiNs, at a different time, or on an entirely different therapeutic schedule (e.g., the CiNs can be administered as needed, while the additional therapeutic agent is administered daily or weekly).

The dosage of CiNs administered to a patient will vary depending on a wide range of factors. For example, it would be necessary to provide substantially larger doses to humans than to smaller animals. The dosage will depend upon the size, age, sex, weight, medical history and condition of the patient, use of other therapies, and the frequency of administration. However, those of ordinary skill in the art can readily determine appropriate dosing, e.g., by initial animal testing, or by administering relatively small amounts and monitoring the patient for therapeutic effect. If necessary, incremental increases in the dose can be administered until the desired results are obtained. Generally, treatment is initiated with smaller dosages which may be less than the optimum dose of the therapeutic agent. Thereafter, the dosage is increased by small increments until the optimum effect under circumstances is reached.

Individuals or subjects in need of the CiNs disclosed herein include, but are not limited to, subjects with a neurodegenerative disorder selected from the group consisting of Alzheimer's Disease (AD), Huntington's Disease (HD), Parkinson's Disease (PD) Amyotrophic Lateral Sclerosis (ALS), Multiple Sclerosis (MS) and Cerebral Palsy (CP), Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Pick's disease, and dentatorubral-pallidoluysian atrophy. Neuronal injury includes, but is not limited to traumatic brain injury, stroke, and chemically induced brain injury. Neuronal injuries can result from any number of traumatic incidents, e.g., obtained in sport, accident, or combat. Neuronal injuries include concussion, ischemia (stroke), hemorrhage, or contusion resulting in damage to the neurons in an individual or significant loss of neuronal tissue in drastic cases. Also included are neuronal injuries and loss caused by pathogenic infection, or chemically induced brain injury, e.g., due to medication, environmental factors, or substance abuse.

Methods for diagnosing neurodegenerative disorders, neurological disorders, and neuronal injuries are known in the art (see, e.g., Diagnostic and Statistical Manual of Mental Disorders, Fourth Edition (DSM-IV-TR), American Psychiatric Assoc. 2000). Generally, a physician or neurologist will consider a number of factors in making a diagnosis in a particular individual or patient. For example, family history is often indicative of a risk of AD, HD, PD, and other neurodegenerative disorders. Doctors will also carry out chemical tests to check for normal blood count, thyroid function, liver function, glucose levels. Spinal fluid is often analyzed as part of this testing. Neuropsychological tests can also be used to assess memory, problem-solving, decision making, attention, vision-motor coordination and abstract thinking. These include spatial exercises and simple calculations. The Mini-Mental State Examination is also common. CAT scans and MRIs can also be used to rule out tumors, and can provide clues as to degraded areas of the brain. Non-invasive medical imaging techniques such as Positron Emisson Tomography (PET) or single photon emission computerized tomography (SPECT) imaging are particularly useful for the detection of brain disease. PET and SPECT imaging shows the chemical functioning of organs and tissues, while other imaging techniques, such as X-ray, CT and MRJ, show structure. The use of PET and SPECT imaging has become increasingly useful for qualifying and monitoring the development of brain diseases. In some instances, the use of PET or SPECT imaging allows a neurodegenerative disorder to be detected several years earlier than the onset of symptoms. Once an individual has been diagnosed as having a deficiency in neuronal cells, e.g., resulting from neurodegeneration or injury, the individual can be considered for treatment with the cell based therapies described herein.

V. Kits

Kits are provided which include a cocktail of the CINPs disclosed herein. The CINPs are as described above. These may be in a form having defined concentrations to facilitate addition to cell culture media to produce a desired concentration. The kit may include directions providing desired concentration ranges and times of administration based on the types of cells to be induced.

The kit may also include cell culture media pre-mixed with the cocktail CINPs for culture of non-neuronal cells to induce neuron-like properties in the non-neuronal cells.

The present invention will be further understood by reference to the following non-limiting examples.

EXAMPLES

Experimental Procedures

Cell Culture

Homozygous TauEGFP knock-in mice (Tucker, et al., Nat Neurosci., 4:29-37 (2001)), FSP1-Cre transgenic mice (Bhowmick, et al., Science, 303:848-851 (2004)) and Rosa-CAG-LSL-tdTomato mice (Madisen, et al., Nat Neurosci., 13:133-140 (2010)) were purchased from Jackson Laboratories. To isolate fibroblasts, TauEGFP heterozygous mice were generated by crossing the homozygous TauEGFP knock-in mice with wild-type mice. FSP1-Cre/ROSA26-tdTomato/TauEGFP mice were generated by crossing the FSP1-Cre transgenic mouse strain, which expresses Cre recombinase under the control of the fibroblast-specific protein 1 (FSP1) promoter (Bhowmick, et al., Science, 303:848-851 (2004); Iwano, et al., J. Clin Invest., 110:341-350 (2002); Strutz, et al., J Cell Biol., 130:393-405 (1995)), with the Rosa26-tdTomato mouse strain (Madisen, et al., Nat Neurosci., 13:133-140 (2010)), in which the Rosa26 locus was inserted using a CAG promoter and was followed by a LoxP-Stop-LoxP cassette-controlled fluorescent tdTomato locus. The resulting mice were further crossed with TauEGFP knock-in mice. Embryonic skin-derived fibroblasts (MEFs) were isolated from E13.5 embryos as previously reported (Vierbuchen et al., Nature, 463:1035-1041 (2010)). All isolated fibroblasts were cultured in fibroblast medium (Dulbecco's Modified Eagle Medium; Hyclone) containing 10% fetal bovine serum (FBS; Hyclone), β-mercaptoethanol (p-ME; Sigma-Aldrich), non-essential amino acids (NEAA; Life Technologies), and penicillin/streptomycin (PS; Life Technologies) and were expanded for 2-3 passages before use.

Generation of CiNs

Small molecules (from Tocris Total) were dissolved and diluted in DMSO according to the manufacturer's instructions and then processed to use at the following final concentrations: ISX9, 20 µM; SB431542, 10 µM; Forskolin, 100 µM; CHIR99021, 20 µM; and I-BET151, 0.5-2 µM. Passaged fibroblasts were seeded onto matrigel-coated plates (BD; 1:30) and were not chemically induced until confluent. The neuronal induction medium (Neurobasal Medium; Life Technologies) contained N2 and B27 supplements, GlutaMAX, PS (all from Life technologies) and bFGF (100-250 ng/ml; Origene). To minimize any potential toxicity of the inducing reagent I-BET151, Y27632 (2 uM) can be used at the early stage of induction (Day 0-4) to enhance the survival rate and reprogramming. After chemical treatment for 20 days, induction medium was changed to maturation medium (induction medium plus forskolin 10 µM, BDNF (Brain-derived neurotrophic factor) 20 ng/ml and GDNF (Glial cell line-derived neurotrophic factor) 20 ng/ml)). The cells were re-plated and co-cultured with primary astrocytes at day 21-35, for further maturation. Culture medium containing the small molecules was refreshed every 3-4 days during the induction period. For the proliferation assay, BrdU (5-bromo-2-deoxyuridine) was added at a final concentration of 10 μM and refreshed in medium.

First-Round Chemical Screening (Ascl1+1)

For Ascl1+1 screening, doxycycline (dox)-inducible Ascl1 lentiviral vector production and infection were performed as previously reported (Vierbuchen, et al., *Nature*, 463:1035-1041 (2010)). Fibroblast medium was supplemented with 2 μg/ml dox (Sigma-Aldrich) after 16-20 hours of infection to activate the expression of exogenous Ascl1. After 48 hours in MEF medium with dox, the cells were transferred to chemically defined neuronal induction medium (Neurobasal Medium; Life Technologies) containing N2 and B27 supplements, GlutaMAX, PS (all from Life technologies) and bFGF (100-250 ng/ml; Origene), and the small molecules for screening was added individually. Medium containing small molecules and dox (2 μg/ml) was refreshed every 3-4 days during the induction period. The small molecule libraries used for chemical screening are shown in Table 1.

TABLE 1

Small-molecule (SM) Libraries CINPs for reprogramming

| LIBRARY | SOURCE | # |
|---|---|---|
| Cell Signaling & Neuroscience Library | National Compound Resource Center | 1,280 |
| Tocriscreen Total | Tocris | 1,120 |
| FDA Approved Drug | National Compound Resource Center | 640 |
| ICCB Known Bioactives | National Compound Resource Center | 480 |
| Natural Products Library | National Compound Resource Center | 502 |
| Protein Kinase Inhibitor I, II, III | Millipore | 324 |
| StemSelect Regulators | Calbiochem | 303 |
| SYN Kinase Inhibitor | National Compound Resource Center | 86 |
| Nuclear Receptor Ligand | Enzo | 76 |
| Selected Small Molecules | Our Lab: Collection of small molecules related to neural development, reprogramming and epigenetic modulation | 56 |

| Full Name/Abbreviation | Conc. (μM) | Source | MW |
|---|---|---|---|
| ISX9 (Isoxazole 9)/I | 10-20 | Tocris, Cat. #4439 | 234.28 |
| Forskolin/F | 50-100 | Enzo, Cat. BML-CN100-0100 | 410.50 |
| CHIR99021/C | 10-20 | Synthesized by WUXI APPTEC | 465.34 |
| I-BET151/B | 2-10 | Synthesized by WUXI APPTEC | 415.44 |
| SB431542/S | 2-10 | Tocris, Cat. #1614 | 384.39 |
| I-CBP112 | 10 | Tocris, Cat. #4891 | 468.59 |
| Bromosporine | 1 | Tocris, Cat. #4758 | 404.44 |
| JQ1 | 1 | Tocris, Cat. #4499 | 456.99 |
| PFI-1 | 5 | Synthesized by WUXI APPTEC | 347.39 |
| Rolipram | 50 | Tocris, Cat. #0905 | 275.35 |
| Dibutyryl-cAMP/DBcAMP | 10 | Santa Cruz, Cat. #sc-201567 | 491.37 |
| 8-Br-cAMP | 200 | Tocris, cat. no. 1140 | 430.08 |
| BIO-acetoxime | 1 | Tocris, cat. no. 3874 | 398.21 |
| GSK3i XV | 0.4 | Santa Cruz, cat. no. sc-221690 | 633.4 |
| SB216763 | 10 | Tocris, cat. no. 1616 | 371.22 |
| Y27632 | 2 | Tocris, cat. no. 1254 | 247.34 |

(amount of SM)
ISX9 = N-Cyclopropyl-5-(2-thienyl)-3-isoxazolecarboxamide
SB431542 = 4-[4-(1,3-benzodioxol-5-yl)-5-(2-pyridinyl)-1H-imidazol-2-yl]benzamide
I-CBP112 = 1-[7-(3,4-Dimethoxyphenyl)-9-[[(3S)-1-methylpiperidin-3-yl]methoxy]-2,3,4,5-tetrahydro-1,4-benzoxazepin-4-yl]propan-1-one;
JQ1 = (6S)-4-(4-Chlorophenyl)-2,3,9-trimethyl-6H-thieno[3,2-f][1,2,4]triazolo[4,3-α][1,4]diazepine-6-acetic acid 1,1-dimethylethyl ester
CHIR99021 ("C") = [6-[[2-[[4-(2,4-Dichlorophenyl)-5-(5-methyl-1H-imidazol-2-yl)-2-pyrimidinyl]amino]ethyl]amino]-3-pyridinecarbonitrile]

Second-Round Chemical screening (FICS+1)

Secondary screening was performed to identify additional small molecules that facilitate neuronal reprogramming and maturation (shown schematically in FIG. 2A). In this screening, the effect of the additional small molecules was evaluated by observing neurite outgrowth. Desirable additional small molecules could induce the neurons with an improved neurite outgrowth as signs of enhanced reprogramming and maturation, ideally with highly complex morphologies. Improved neurite morphologies were evaluated in terms of enhanced neurite branches and neurite length. Further, characterization (e.g. TUJ1 immunostaining) was performed to confirm the observation. Fibroblasts were seeded into 12-well plates and each additional small molecule was added well by well into the culture medium containing the basic small-molecule cocktail (SM-cocktail+1 Screening), while SM-cocktail+DMSO was used as a negative control. In a 16-day induction period, the culture medium was refreshed every 3-4 days during the induction period and the additional small molecules that obviously enhanced the outgrowth of neuritis were regarded as the candidates. By screening about 1,500 small molecules, an additional small molecule, I-BET151, which dramatically enhanced the reprogramming rate and neurite outgrowth of the induced neurons by observation, which was further confirmed by immunostaining (FIGS. 2B and 2C, Table 1), was identified. TUJ1-positive cells with circular cell bodies and neurite outgrowth that is at least three-fold longer than the cell body were quantified. Ten randomly selected visual fields (20×) were used to determine the cell number.

Immunofluorescence

Cells were washed with PBS twice and then fixed with 4% paraformaldehyde for 20 min at room temperature. Afterward, the cells were washed with PBS twice and then blocked and permeabilized with 0.25% PBST (PBS plus 0.25% Triton X-100) and 3% donkey serum (DS) for 1 hour at 37° C. A PAP pen was used to outline the fields for staining. Diluted primary antibodies were added to the outlined fields, and the samples were incubated at 4° C. overnight. Next, the cells were washed three times with PBS and incubated in PBS plus 3% DS with diluted secondary antibodies for 1 hour at room temperature. The nuclei of the cells were stained with DAPI (Roche Molecular Biochemicals) if needed. The following primary antibodies were used in this study: rabbit anti-TUJ1 (Covance, 1:500), mouse anti-TUJ1 (Santa Cruz, 1:100), mouse anti-MAP2 (Sigma-Aldrich, 1:200), rabbit anti-NF-H (Abcam, 1:500), mouse anti-NeuN (Millipore, 1:50), rabbit anti-GABA (Sigma-Aldrich, 1:10,000), rabbit anti-vGLUT1 (Synaptic Systems, 1:5,000), rabbit anti-COL1A1 (Abcam, 1:500), mouse anti-BrdU (Santa Cruz, 1:50), goat anti-SOX2 (Santa Cruz, 1:100), rabbit anti-PAX6 (Covance, 1:250), rabbit anti-GFAP (Dako, 1:400), mouse anti-A2B5 (Millipore, 1:200), goat anti-SOX10 (Santa Cruz, 1:20), and rabbit anti-P75 (Millipore, 1:100). The following secondary antibodies were used in this study: FITC and TRITC-conjugated secondary antibodies (Jackson ImmunoResearch) and Alexa Fluor 647-conjugated secondary antibodies (Life Technologies).

RT-Quantitative PCR

Total RNA was extracted using the Qiagen RNeasy Plus mini kit and was reverse transcribed into cDNA with TransScript One-step gDNA Removal and cDNA Synthesis SuperMix (TransGen Biotech). Real-time PCR was performed using a 7300 Real-Time PCR system (Applied Biosystems) with Power SYBR Green PCR Master Mix (2×). The primers used are listed in Table 2.

TABLE 2

Primers for RT-quantitative PCR.

| GENE NAME | FORWARD (5' TO 3') | REVERSE (5' TO 3') | APPLICATION |
| --- | --- | --- | --- |
| Gapdh | CATGTTCCAGTATGACTCCACTC (SEQ ID NO: 1) | GGCCTCACCCCATTTGATGT (SEQ ID NO: 2) | single cell analysis real-time qPCR |
| β3-actin | ATCTTCCGCCTTAATACTTCATTT (SEQ ID NO: 3) | TGCCTCAACACCTCAACCC (SEQ ID NO: 4) | real-time qPCR |
| NF-H | CTGACAGATGACCGCAATAATGAA (SEQ ID NO: 5) | GCAAGGGCCTGACCACTCCT (SEQ ID NO: 6) | single cell analysis |
| Ascl1 | ACTTGAACTCTATGGCGGGTT (SEQ ID NO: 7) | CCAGTTGGTAAAGTCCAGCAG (SEQ ID NO: 8) | real-time qPCR |
| Ngn2 | TGGCTGGCATCTGCTCTATT (SEQ ID NO: 9) | TAGGCATTGTGACGAATCTG (SEQ ID NO: 10) | real-time qPCR |
| Brn2 | GACAAGATCGCAGCGCAAGG (SEQ ID NO: 11) | GGCTTAGGGCATTTGAGGAA (SEQ ID NO: 12) | real-time qPCR |
| Myt1l | CAGGAGTCAGCCACCCAACA (SEQ ID NO: 13) | TCCAGCCGCATAAGGTTCAT (SEQ ID NO: 14) | real-time qPCR |
| NeuroD1 | ACGCAGAAGGCAAGGTGTCC (SEQ ID NO: 15) | GTTCCTCGTCCTGAGAACTG (SEQ ID NO: 16) | real-time qPCR |
| Olig2 | GGCGGTGGCTTCAAGTCAT (SEQ ID NO: 17) | CATGGCGATGTTGAGGTCG (SEQ ID NO: 18) | real-time qPCR |
| Prrx1 | AGTCACCGGGACTGACCA (SEQ ID NO: 19) | TCCGCTGCTTTCTCTTCTTC (SEQ ID NO: 20) | real-time qPCR |
| OSR1 | CTCTGGTCACTCAAGTCCAGC (SEQ ID NO: 21) | ATTTCTGTCGCTGGGAACC (SEQ ID NO: 22) | real-time qPCR |
| Twist2 | GTCTCAGCTACGCCTTCTCC (SEQ ID NO: 23) | GCCTGAGATGTGCAGGTG (SEQ ID NO: 24) | real-time qPCR |

TABLE 2-continued

Primers for RT-quantitative PCR.

| GENE NAME | FORWARD (5' TO 3') | REVERSE (5' TO 3') | APPLICATION |
| --- | --- | --- | --- |
| Lhx9 | TCTTGCAAGGGGAATATCCA (SEQ ID NO: 25) | GTGCCAGTGCCATTGAAGTA (SEQ ID NO: 26) | real-time qPCR |
| Snail1 | CTTGTGTCTGCACGACCTGT (SEQ ID NO: 27) | AGTGGGAGCAGGAGAATGG (SEQ ID NO: 28) | real-time qPCR |
| Zeb1 | CCAGGTGTAAGCGCAGAAAG (SEQ ID NO: 29) | TCATCGGAATCTGAATTTGC (SEQ ID NO: 30) | real-time qPCR |
| Thy1 | AACTCTTGGCACCATGAACC (SEQ ID NO: 31) | GTCAGGCTGGTCACCTTCTG (SEQ ID NO: 32) | real-time qPCR |
| Synapsin I | TCTTCCTCCAACCTCCACTCCT (SEQ ID NO: 33) | TGGGCCTTTGCTTGTTTATTTT (SEQ ID NO: 34) | single cell analysis |
| VGlut | TGTTGGGTTTGGGGATT (SEQ ID NO: 35) | AGGTTTTATGCTTTGCACTTA (SEQ ID NO: 36) | single cell analysis |
| Gad67 | CACAAACTCAGCGGCATAGA (SEQ ID NO: 37) | CTGGAAGAGGTAGCCTGCAC (SEQ ID NO: 38) | single cell analysis |
| NeuN | ACAGACAACCAGCAACTCCA (SEQ ID NO: 39) | CCGAATTGCCCGAACAT (SEQ ID NO: 40) | single cell analysis |
| Col1a1 | CATGTTCAGCTTTGTGGACCT (SEQ ID NO: 41) | GCAGCTGACTTCAGGGATGT (SEQ ID NO: 42) | single cell analysis |
| Fsp1 | GTGTCCACCTTCCACAAATACTCA (SEQ ID NO: 43) | ACTTCATTGTCCCTGTTGCTGTC (SEQ ID NO: 44) | single cell analysis |
| Htr2c | GCTGGACCGGTATGTAGCAA (SEQ ID NO: 45) | GCTTTCGTCCCTCAGTCCAA (SEQ ID NO: 46) | single cell analysis |
| Tph1 | TGGAGGAAGGACTGAGAGGA (SEQ ID NO: 47) | TTTCGGAGGAATGGTCTTTG (SEQ ID NO: 48) | single cell analysis |
| Periperin | CTCAGTGCCGGTTCATTCCT (SEQ ID NO: 49) | TCTGTCACCACCTCCCCATC (SEQ ID NO: 50) | single cell analysis |
| Th | CACTATGCCCACCCCCAG (SEQ ID NO: 51) | CGCCGTCCAATGAACCTT (SEQ ID NO: 52) | single cell analysis |
| Ddc | ACAAGTGGCTTTTGGTGAACT (SEQ ID NO: 53) | TCCTGGTGACTGTGCTTTAGA (SEQ ID NO: 54) | single cell analysis |
| Dlx5 | CTACAACCGCGTCCCGAG (SEQ ID NO: 55) | GATTTTCACCTGTGTTTGCGTCAG (SEQ ID NO: 56) | single cell analysis |
| Darpp32 | CCACCCAAAGTCGAAGAGAC (SEQ ID NO: 57) | GAGGCCTGGTTCTCACTCAA (SEQ ID NO: 58) | single cell analysis |
| Tpm2 | AAGGATGCCCAGGAGAAACT (SEQ ID NO: 59) | CCGATCCAACTCCTCCTCTAC (SEQ ID NO: 60) | single cell analysis |
| Pcp2 | GCCTGGCTTCCAACCTATC (SEQ ID NO: 61) | GAAGCTGAGTGCAGCAGGAT (SEQ ID NO: 62) | single cell analysis |
| Pclo | AAAGGGGCTCATGCTCACTC (SEQ ID NO: 63) | GGTGAGAGGCAGTCTTGGAC (SEQ ID NO: 64) | single cell analysis |
| Bsn | CAGCTCTGGACTCTGCGTAT (SEQ ID NO: 65) | TAGGTCGCTGCTGTGAGAAC (SEQ ID NO: 66) | single cell analysis |
| Shank3 | AGGAACTTGCTTCCATTCGGA (SEQ ID NO: 67) | CCTCGAGTCAGCATCTGCAA (SEQ ID NO: 68) | single cell analysis |
| Unc5d | CAAAATCTGCATTCGGCAGC (SEQ ID NO: 69) | GGTACTGTCCTCTTGTGCGA (SEQ ID NO: 70) | single cell analysis |
| Mel2c | AGTTTGGACAACAAAGCCCTC (SEQ ID NO: 71) | CATTGGCCTTCCACGCTTC (SEQ ID NO: 72) | single cell analysis |
| Etv1 | TTAAGTGCAGGCGTCTTCTTC (SEQ ID NO: 73) | GGAGGCCATGAAAAGCCAAA (SEQ ID NO: 74) | single cell analysis |

TABLE 2-continued

Primers for RT-quantitative PCR.

| GENE NAME | FORWARD (5' TO 3') | REVERSE (5' TO 3') | APPLICATION |
|---|---|---|---|
| Syt9 | CGAGAGCATCGACCAGATCC (SEQ ID NO: 75) | AGCCTCGTTTCCTACTTGGC (SEQ ID NO: 76) | single cell analysis |
| Pcp4 | TGAGCTGTTCTGTGGGACCT (SEQ ID NO: 77) | TTGTCTTTTCCGTTGGTCGCT (SEQ ID NO: 78) | single cell analysis |
| Tle4 | AAGATGTACCCGCAGACGC (SEQ ID NO: 79) | AGCTTCTCACATTCCAGCTTCA (SEQ ID NO: 80) | single cell analysis |
| Crim1 | GGTACCATCCGAACCTGCAA (SEQ ID NO: 81) | GGAGAGAACCGCACTTCACA (SEQ ID NO: 82) | single cell analysis |
| Nr4a3 | AGGATTCACTGATCTCCCCAA (SEQ ID NO: 83) | GATGCAGGACAAGTCCATTGC (SEQ ID NO: 84) | single cell analysis |
| Tbr1 | ACAATGGGCAGATGGTGGTT (SEQ ID NO: 85) | GTGTCCTCTGTGCCATCCTC (SEQ ID NO: 86) | single cell analysis |
| Dcx | TTCAGGACCACAAGCAATGA (SEQ ID NO: 87) | GGAAACCGGAGTTGTCAAAA (SEQ ID NO: 88) | single cell analysis |
| Dbh | GGGGGACGTACTCATCACTT (SEQ ID NO: 89) | CAGCTCTGTCTGGGGGTAGT (SEQ ID NO: 90) | single cell analysis |

Gene expression was analyzed using the ΔΔCt method. All the results were normalized to β-actin expression, and the values of uninduced fibroblasts were set to 1. Two replicates were used to determine the error bars.

Flow Cytometry

The efficiency of the production of TAU-EGFP-positive cells was estimated using a FACSCalibur flow cytometer (Becton Dickinson), and the flow cytometry data were analyzed using FlowJo. Purification of tdTomato-positive cells was performed using a MoFlo cell sorter (Dako Cytomation).

Single-Cell Gene Expression Analysis

Single cells were selected with disposable glass capillaries (single use), and the transcripts of the cell were captured carefully following the standard protocol (Tang, et al., Nat. Protoc., 5:516:535 (2010)). Next, single-cell cDNA products were prepared using a Power SYBR® Green Master Mix kit (Life Technologies) according to the manufacturer's instructions and then processed for real-time PCR analysis on a 7300 real-time PCR system (Applied Biosystems). The data were analyzed using the software associated with the PCR system, and the melting curves were carefully examined to assess the specificity of each reaction. The cycle threshold (Ct) values were calculated and used to determine the single-cell gene expression profiles (blue to red as given). The primers used are listed in Table 2.

Primary Neuron Culture and iN Replating

Primary cultures of neurons were prepared from postnatal day 1 wild-type C57 mice. Mice were decapitated, and their brains were removed in pre-cooled physiological saline. The hippocampus was dissected in pre-cooled HBSS (9.5 g/L Hanks' balanced salts, 4.2 mM NaHCO$_3$, 10 mM HEPES, 12 mM MgSO$_4$, 7 g/L glucose, 0.3 g/L bull serum albumin, and 0.5% penicillin/streptomycin, with the pH adjusted to 7.4 with NaOH). Tissues were digested with 5 ml 0.2% trypsin (Gibco, dissolved in digestion solution) for 2-3 min, and the digestion reaction was stopped with 1 mg/ml trypsin inhibitor (Sigma, dissolved in HBSS). The digestion solution contained (in mM) 4.2 NaHCO$_3$, 25 HEPES, 137 NaCl, 5 KCl, and 7 Na$_2$HPO$_4$, and the pH was adjusted to 7.4 with NaOH. The cells were washed three times and centrifuged for 10 min at 1,000 rpm. The neurons were resuspended in Dulbecco's Modified Eagle Medium (DMEM, pH adjusted to 7.4 with NaOH) containing 3.7 g/L NaHCO$_3$, 10 mM HEPES, 1% penicillin/streptomycin (Invitrogen), 2% B27 supplement (Invitrogen) and 10% fetal bovine serum (Hyclone). A total of 5×10$^5$ cells were plated onto 10×10 mm coverslips that had been pre-treated with 12.5 μg/ml poly-D-lysine and were incubated in 24-well plates. The plates were incubated at 37° C. in a 5% CO$_2$/95% air incubator for 4-6 h, and the medium was replaced with Neurobasal (Invitrogen) medium containing 2% B27 supplement, 2 mM glutamine and 0.5% penicillin/streptomycin. Half of the medium was changed every three days. One week after primary neuron plating, the iNs (induced neurons/neuron-like cells; before being replated onto primary neurons for further maturation, the induced cells from fibroblasts are immature neuronal-like cells) were gently removed from the dishes by pipetting the medium and were replated onto primary neurons. Electrophysiological recordings were performed between day 10 and day 14 after replating.

RNA-Seq

Total mRNA was isolated from fibroblasts, CiNs (48 hours and 19 day-induced) and primary neurons. RNA sequencing libraries were constructed using the Illumina mRNA-seq Prep Kit. The fragmented and randomly primed 200-bp paired-end libraries were sequenced using Illumina HiSeq 2000. The transcriptome reads were mapped using the TopHat program. Normalized differentially expressed (DE) genes were detected. The RPKM values were used to evaluate the expression levels of genes. Hierarchical clustering was conducted by Cluster 3.0 and TreeView. In the scatter plot, a 2 fold-change threshold cutoff was set as significantly changed gene expressions. Gene ontology analysis of the DE genes was performed using the DAVID program which is described in Nature Protoc., 4(1):44-57 (2009).

Accession Numbers

The GEO accession number for RNA-Seq data in this study is GSE68715.

Electrophysiology

For whole-cell patch-clamp recordings, the ACSF (artificial cerebrospinal fluid) extracellular solution contained (in mM) 141 NaCl, 2.5 KCl, 1.3 $MgCl_2$, 2.4 $CaCl_2$, 1.25 $NaH_2PO4$ 10 glucose and 10 HEPES (pH adjusted to 7.4 with NaOH), and the internal pipette solution contained (in mM) 140 potassium gluconate, 1 $CaCl_2$, 10 EGTA, 2 $MgCl_2$, 10 HEPES, and 5 $Na_2ATP$ (pH adjusted to 7.3 with KOH). Patch pipettes were pulled with a P97 micropipette puller (Sutter Instruments) to achieve a ~5 MΩ tip resistance. Patch-clamp recordings were taken using an EPC-10 amplifier (HEKA) with PatchMaster. To record the sodium and potassium currents, cells were held at −80 mV and depolarized from −80 to +80 mV in 10 mV increments for 1 s. The sample and sweep intervals were 20 is and 2 s, respectively. Tetrodotoxin (TTX; 10 µM) dissolved in extracellular solution was applied with an ALA-VM4 valve manifold (Scientific Instruments), and washout from the iNs was assessed to determine whether the inward fast inactivating current was a sodium current. For current-clamp recordings, a hyperpolarized current was injected into iNs to membrane potentials around −70 mV. The current was ramped to 500 pA to elicit action potentials (APs) for the calculation of the AP thresholds and amplitudes. Step-depolarized currents were injected to elicit action potentials with sweep intervals of 3 s. The cells were held at 0 pA to record the resting membrane potentials. In current-clamp mode, the sample frequency was 25 kHz. To record spontaneous excitatory postsynaptic currents (sEPSCs) and spontaneous inhibitory postsynaptic currents (sIPSCs), the iNs were held at −70 mV (close to the reversal potential of chloride) and 0 mV, respectively. The data were continuously digitized at 20 kHz.

Results

Small-Molecule Screening for Compounds Inducing Neuronal Fate

To identify the neuronal-fate-inducing small molecules, a primary chemical screen of small molecules was performed. A set of three transcription factors (Ascl1, Brn2 and Myt1l) has been shown to induce the generation of neurons from mouse fibroblasts, in which Ascl1 is the master gene for inducing neuronal fate, while Brn2 and Myt1l enhance the neuronal conversion as the supplementary factors (Vierbuchen et al., Nature, 463:1035-1041 (2010)). Without Brn2 and Myt1l, Ascl1 alone induces neurons with low efficiency (Vierbuchen et al., Nature, 463:1035-1041 (2010)). A chemical screen for small molecules promoting the Ascl1-based conversion was first performed. The screen was carried out on mouse embryonic skin-derived fibroblasts (MEFs) isolated from Tau-EGFP knock-in reporter mice and the MEFs were infected with viruses expressing Ascl1 (Tucker et al., Nat Neurosci., 4:29-37 (2001); Vierbuchen et al., Nature, 463:1035-1041 (2010)) (FIG. 1A). By screening about 5,000 small molecules (Table 1), Forskolin, ISX9, CHIR99021, and SB431542 were identified, each increasing the number of TAUEGFP-/TUJ1-positive neuronal cells induced by Ascl1 to more than 2-fold (FIG. 1B).

Figure 1B:
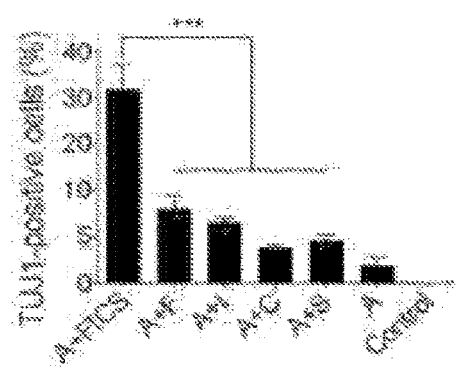
FIG. 1B shows quantification of TUJ1-positive cells with circular cell bodies and neurite outgrowth that is at least three-fold longer than the cell body. Ten randomly selected visual fields (20×) were used to determine the cell number, and the graph represents the percentage of the qualified TUJ1-positive cells relative to DAPI-stained cells.

In the presence of Ascl1, the combination of these four chemical boosters further increased the efficiency of generating induced neurons (iNs) (>10-fold enhancement than Ascl1 infection alone without compounds, total >30% yield after 8 days of induction) (FIG. 1B). Thus, a combination of four small molecules that robustly facilitate the Ascl1-mediated induction of neuronal fates from mouse fibroblasts was identified.

Figure 1C:
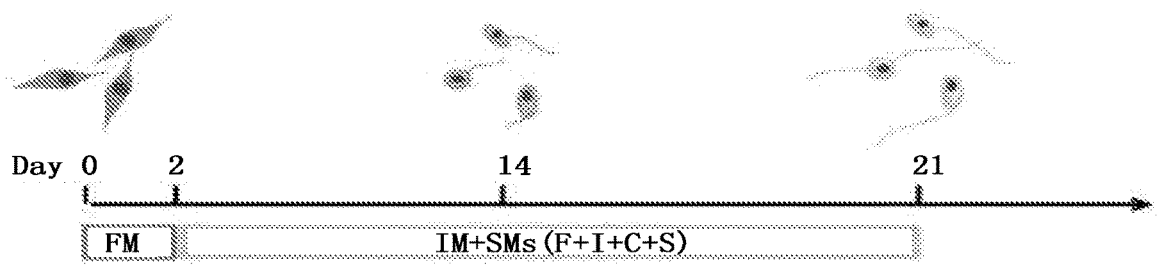
FIG. 1C is a schematic showing SM induction process. FM, fibroblast medium; IM, neuronal induction medium.
Figure 1D:
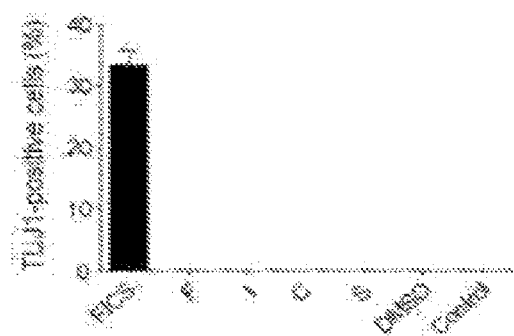
FIG. 1D shows quantification of TUJ1-positive cells induced by SMs (ten 20× visual fields were randomly selected to determine the number relative to DAPI-stained cells). A, Ascl1; Control, not induced; S, SB431542; C, CHIR99021; I, ISX9; F, forskolin; DMSO, vehicle control. The data are presented as the mean+/−SEM. *P<0.05; P<0.01; *P<0.001 (Student's t-test).

To examine whether the exogenous "master genes" are dispensable for inducing neuronal fates, the starting fibroblasts were induced in a transgene-free manner (FIG. 1C). In the absence of exogenous Ascl1, the culture medium containing the four small-molecule cocktail "FICS" (Forskolin, ISX9, CHIR99021 plus SB431542) sufficed to induce neuronal fate in an extended duration (21 Days) with a >30% yield of TUJ1-positive cells with primitive neuronal-like morphology (FIG. 1C-D and Table 1). Each small molecule alone failed to generate neuronal-like cells as measured by TUJ1-positive cells, suggesting a synergism between the small molecules may be crucial (FIG. 1F). These findings show that the novel small-molecule cocktail can initiate neuronal fates from fibroblasts.

Identification of I-BET151 Facilitated Chemical Reprogramming

Figure 2J:
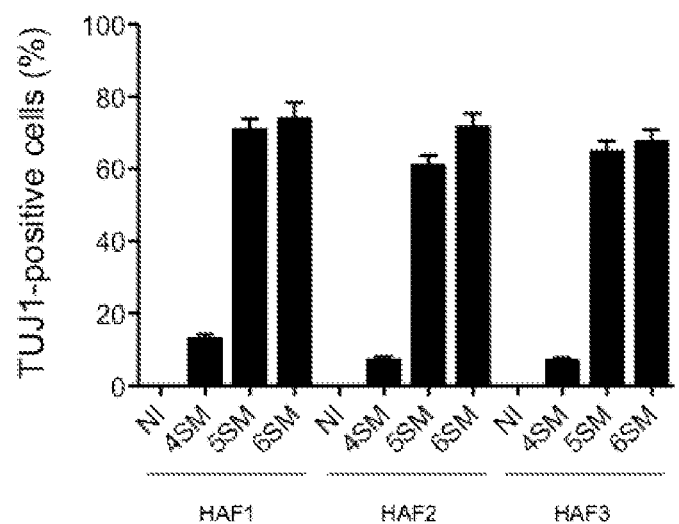
FIG. 2J is a bar graph showing quantification of TUJ1-positive cells with circular cell bodies and neurite outgrowth that is at least three-fold longer than the cell body. Ten randomly selected visual fields (20×) were used to determine the cell number, and the graph represents the percentage of TUJ1-positive cells relative to DAPI-stained cells. The data are presented as the mean+/−SEM. *P<0.05; ***P<0.001 (Student's t-test).

To improve the transgene-free chemical induction into a more robust system, another chemical screen for additional small molecules that facilitate neuronal reprogramming and maturation was performed (FIG. 2A). This further screen aimed to identify additional small molecules that could induce non neuronal cells into neuron-like cells with an improved neurite outgrowth, and preferably, having more complex neuron-like morphologies. I-BET151 was identified as a hit that dramatically enhanced the reprogramming rate (with a 90% TUJ1-positive cells yield) and neurite outgrowth of the induced neurons (data not shown and Table 1), by screening about 1,500 additional small molecules. Moreover, in the new cocktail, FICSB, SB431542 (S) was dispensable for generating neurons, although it enhanced the survival and neurite outgrowth of the induced neurons (FIG. 2B). The small molecule cocktail FICB was then used in further experiments, and the concentration of each small molecule was further optimized (FIGS. 2F-I). The FICB cocktail converted mouse fibroblasts into neuron-like cells with a yield up to >90% TUJ1-positive cells (in which 71% TAUEGFP/TUJ1-double positive and 30% NeuN/TUJ1-double positive) with extensive neurite outgrowth after 16-20 days of induction (FIG. 2B-2D). The FICB-induced cells co-expressed multiple neuronal-specific markers, including MAP2 and NF-H (data not shown). Furthermore, the FICB-induced cells seemed to be heterogeneously excitatory and inhibitory, which was supported by the detection of both VGLUT1- and GABA-positive neurons (data not shown). The small molecule cocktail identified herein similarly induced reprogramming of human fibroblasts into neuron-like cells. Human fibroblasts were transduced with a Synapsin-red fluorescent protein (RFP) reporter construct to identify desirable functional neurons. After chemical induction, Synapsin-RFP positive cells with neuronal morphology could be identified, indicating that were efficiently induced into neuron-like cells. Upon the chemical induction for 16-20 days, the yield of the TUJ1-double positive cells generated from human fibroblasts reached >60% (FIG. 2J) (identified by co-immunostaining Synapsin-RFP for TUJ1). Furthermore, the induced Synapsin-RFP positive cells from human fibroblasts co-expressed neuron-specific markers MAP2 and GABA (γ-amino butyric acid) (data not shown).

Taken together, these results show chemical reprogramming of non-neuronal cells into cells with neuron-like properties using the additional small molecule, I-BET151. Enhancing reprogramming with I-BET151 resulted in some toxicity; however, treating the cells being induced with Y2632 (M) (from Day 0 to about day 4) enhanced the survival rate and reprogramming.

Gene Expression Profiling of CiNs Resembles Functional Neurons

To further promote the maturation of the induced neurons, co-culturing the induced cells with primary astrocytes in the maturation medium was employed as reported (Chanda et al., *Stem Cell Reports*, 3:282-296 (2014); Vierbuchen et al., *Nature*, 463:1035-1041 (2010)). After promoting maturation for 14-21 days, the induced cells further gained more extensively extended neurite outgrowth. The induced cells expressed mature neuronal marker, NeuN (data not shown). These chemically-induced neurons were then referred to as CiNs (FIG. 2E). To ensure the co-expression of neuronal and functional subtype-specific markers and preclude the noise of a mixed cell population, single-cell expression profiling was performed on the CiNs. Multiple pan-neuronal and functional synaptic markers were co-expressed in single induced cell (data not shown). Both excitatory and inhibitory subtypes of single induced neuronal-like cell were detected. The majority of the CiNs are the excitatory, glutamatergic neurons (about 45.8%), as indicated by the expression of vGlut, and the percentage of the inhibitory subtype is about 20.8%, as indicated by the expression of Gad67. Furthermore, the induced cells not only established a neuron-specific transcriptional program (synapsin 1, Gad67, vGlut, and NF-H), but also down-regulated the expression of fibroblast-specific genes, Fsp1 and Col1a1 (data not shown).

Electrophysiological Function of CiNs

Figure 3A:
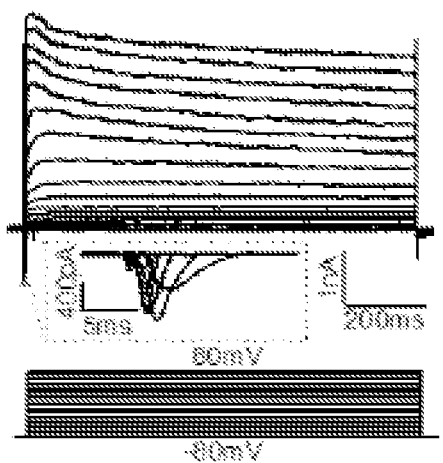
FIGS. 3A-E show functional properties (electrophysiological) of CiNs.

To determine the electrophysiological functional properties of the CiNs, whole-cell patch-clamp recordings were performed. By depolarizing the membrane in current-clamp mode, action potentials (APs) were elicited on the CiNs with extending branches (35.0%, n=20) after 14-20 days of chemical induction (FIG. 3A). The electrophysiological properties of induced neurons are shown in Table 3.

TABLE 3

Electrophysiological properties of induced neurons before co-culture

| Induction | Rm (GO) | Cm (pF) | RMP (mV) | APthreshold (mV) | APamp (mV) | Ina-max(pA) | N |
| --- | --- | --- | --- | --- | --- | --- | --- |
| CiNs | 0.404 ± 0.068 | 12.422 ± 1.225 | −21.861 ± 3.563 | −35.739 ± 2.225 | 48.753 ± 4.462 | −838.513 ± 174.686 | 7/20 |
| Cell1 | 0.19 | 14.65 | −29.99 | −40.68 | 38.65 | −1216.17 | 1/20 |
| Cell2 | 0.36 | 9.01 | −18.40 | −33.54 | 51.51 | −399.09 | 1/20 |
| Cell3 | 0.71 | 11.93 | −28.40 | −35.88 | 49.46 | −1049.08 | 1/20 |
| Cell4 | 0.52 | 17.28 | −35.59 | −41.57 | 55.68 | −438.37 | 1/20 |
| Cell5 | 0.33 | 10.94 | −13.99 | −32.57 | 37.46 | −646.98 | 1/20 |
| Cell6 | 0.23 | 14.66 | −10.47 | −40.74 | 64.00 | −1610.73 | 1/20 |
| Cell7 | 0.48 | 8.50 | −16.20 | −25.30 | 34.33 | −509.17 | 1/20 |

Rm: input resisitance;
Cm: membrane capacitance;
RMP: resting membrane potential;
APthreshold: action potential threshold;
APamp: action potential amplitude;
Ina-max: maximum amplitude of sodium current.
All the data are mean +/− SEM.

Figure 3B:
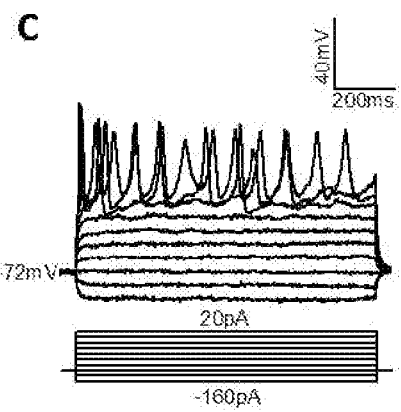
Figure 3C:
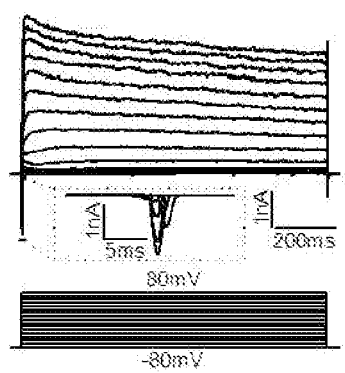
Figure 3D:
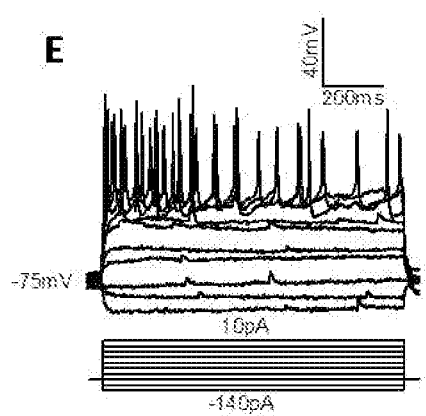

Furthermore, fast, inactivating inward and outward currents were recorded on the CiNs in the voltage-clamp mode, which may correspond to the opening of voltage-dependent $K^+$- and $Na^+$-channels (FIG. 3B; Table 3). Accordingly, when re-plated onto a pre-existing monolayer culture of primary astrocytes or primary neurons, functional membrane properties of the CiNs were significantly enhanced (53.8%, n=39) (FIG. 3C, 3D and Table 4). The electrophysiological properties of CiNs following co-culture are shown in Table 4.

TABLE 4

Electrophysiological properties of CiNs co-culturing with primary astrocytes or primary neurons

| Induction | Rm (GO) | Cm (pF) | RMP (mV) | APthreshold (mV) | APamp (mV) | Ina-max(pA) | N |
| --- | --- | --- | --- | --- | --- | --- | --- |
| CiNs (Co-cultured) | 0.544 ± 0.0900.568 ± 0.093 | 17.921 ± 4.313 | −35.927 ± 2.897 | −31.686 ± 1.865 | 55.990 ± 3.802 | −2865.697 ± 908.167 | 21/39 |
| Cell1 | 0.76 | 6.78 | −30.95 | −41.15 | 75.91 | −1508.30 | 1/39 |
| Cell2 | 0.44 | 8.18 | −23.88 | −36.04 | 36.79 | −425.66 | 1/39 |
| Cell3 | 1.45 | 8.85 | −45.86 | −25.59 | 27.55 | −310.20 | 1/39 |
| Cell4 | 0.31 | 11.47 | −29.49 | −36.36 | 50.47 | −1056.07 | 1/39 |
| Cell5 | 1.20 | 9.41 | −46.21 | −31.51 | 36.69 | −631.25 | 1/39 |
| Cell6 | 0.42 | 9.37 | −32.20 | −39.43 | 62.68 | −1076.39 | 1/39 |
| Cell7 | 1.02 | 7.07 | −41.06 | −23.84 | 32.87 | −381.63 | 1/39 |
| Cell8 | 0.39 | 8.12 | −16.32 | −34.64 | 53.03 | −850.53 | 1/39 |
| Cell9 | 0.29 | 7.42 | −27.84 | −27.83 | 67.41 | −1898.94 | 1/39 |
| Cell10 | 0.49 | 9.88 | −25.63 | −35.72 | 46.92 | −296.19 | 1/39 |

TABLE 4-continued

Electrophysiological properties of CiNs co-culturing with primary astrocytes or primary neurons

| Induction | Rm (GO) | Cm (pF) | RMP (mV) | APthreshold (mV) | APamp (mV) | Ina-max(pA) | N |
|---|---|---|---|---|---|---|---|
| Cell11 | 0.66 | 6.72 | −31.63 | −33.76 | 54.81 | −470.67 | 1/39 |
| Cell12 | 0.49 | 7.64 | −36.02 | −35.65 | 53.79 | −931.66 | 1/39 |
| Cell13 | 0.53 | 10.39 | −29.99 | −15.41 | 51.04 | −1473.80 | 1/39 |
| Cell14 | 0.19 | 7.69 | −35.16 | −18.43 | 39.27 | −1002.77 | 1/39 |
| Cell15 | 0.35 | 10.36 | −24.80 | −30.54 | 51.74 | −1967.50 | 1/39 |
| Cell16 | 0.10 | 10.15 | −19.89 | −15.62 | 63.24 | −1967.50 | 1/39 |
| Cell17 | 0.10 | 34.67 | −54.06 | −44.10 | 90.51 | −9655.18 | 1/39 |
| Cell18 | 0.29 | 33.34 | −53.75 | −31.37 | 69.14 | −11444.30 | 1/39 |
| Cell19 | 0.32 | 54.06 | −32.48 | −40.70 | 67.60 | −5981.56 | 1/39 |
| Cell20 | 0.30 | 76.63 | −53.42 | −30.17 | 59.70 | −4577.51 | 1/39 |
| Cell21 | 1.33 | 38.14 | −63.81 | −37.56 | 84.64 | −13663.20 | 1/39 |

All the data are mean +/− SEM.

Figure 3E:
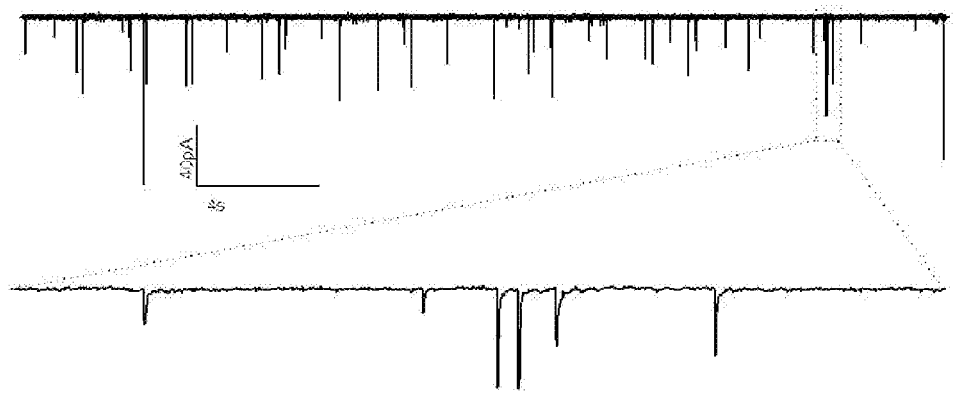

Spontaneous excitatory postsynaptic currents (EPSCs) could be recorded on the CiNs after re-plating (47.6%, n=21) (FIG. 3E; Table 4 and data not shown). The EPSCs could be blocked by the specific receptor antagonists, 6-cyano-7-nitroquinoxaline-2,3-dione (CNQX) and 2-amino-5-phosphonovaleric acid (AP5) (data not shown).

These results are indicative of functional membrane properties in CiN cells. Furthermore, after development by co-culturing with primary astrocytes or primary neurons, the CiNs are capable of forming functional synaptic connection with each other or the pre-existing primary neurons.

Lineage Tracing to Confirm the Fibroblast-to-Neuron Chemical Reprogramming

Figure 4A:
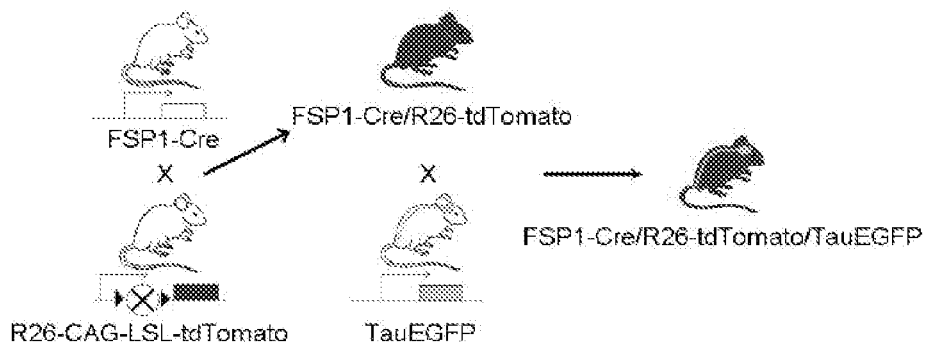
FIG. 4A is a schematic showing the experimental rationale for the proposed genetic lineage tracing system.
Figure 4B:
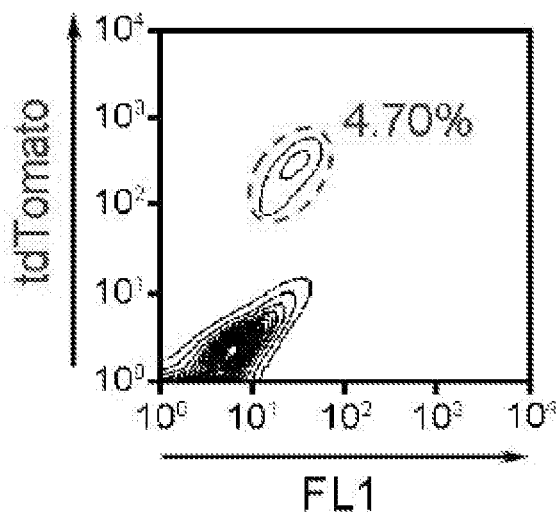
FIG. 4B is a graphs showing purification of tdTomato-positive MEFs by FACS.
Figure 4C:
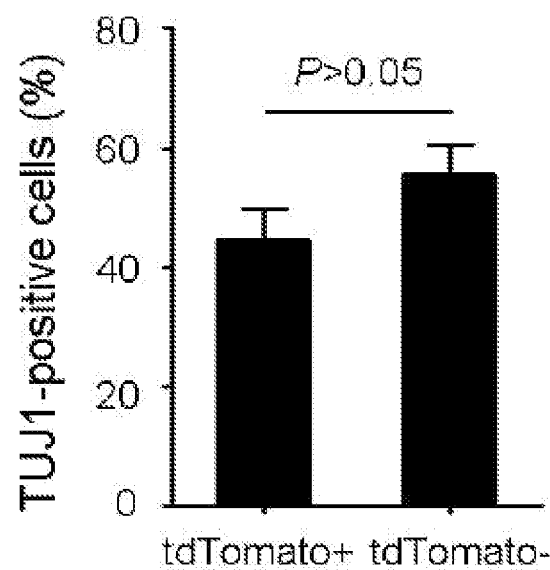
FIG. 4C shows quantification of TUJ1-positive cells induced from tdTomato-positive and -negative cells. (F-H) TAUEGFP/tdTomatodouble-positive cells co-expressed TUJ1 (F), MAP2 (G), and NF-H (H). The data are presented as the mean+/−SEM.

To confirm the fibroblast origin of the initial cell culture, a Cre-LoxP lineage tracing system was employed to trace the fate of original fibroblasts expressing a fibroblast-specific gene, Fsp1 (Bhowmick, et al., *Science*, 303:848-851 (2004); Iwano, et al., *J Clin Invest.*, 110:341-350 (2002); Madisen, et al., *Nat Neurosci.*, 13:133-140 (2010); Strutz, et al., *J Cell Biol.*, 130:393-405 (1995)) (FIG. 4A). TdTomato-positive cells were further confirmed by co-immunostaining with another fibroblast marker, COLIA1 (FIG. 4B and data not shown). After the chemical induction, the tdTomato-positive cells developed extensive branch outgrowth (data not shown). The data shows that tdTomato-positive cells could be chemically reprogrammed into neuronal cells with a comparatively high efficiency (FIG. 4C). This result provides direct genetic proof of the chemical reprogramming of fibroblasts into neurons.

CiNs Generation is Direct without an Intermediated Proliferative Stage

Figure 4D:
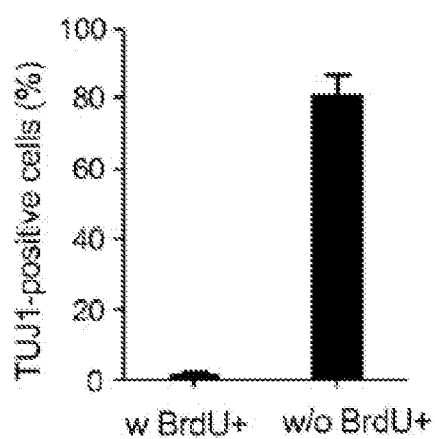
FIG. 4D shows quantification of the rate of BrdU incorporation in CiNs after reprogramming. Five random visual fields (20×) were selected for each replicate, and the cell counts were determined using two replicates for each condition. The data are presented as the mean+/−SEM

To further understand the reprogramming process, the cells were treated with 5-bromodeoxyuridine (BrdU) with the small-molecule induction and throughout the culture period for chemical reprogramming (Vierbuchen et al., *Nature*, 463:1035-1041 (2010)). The results show that the vast majority (about 80%) of the TUJ1-positive iNs did not incorporate BrdU (FIG. 4D), indicating a direct cell fate reprogramming bypassing an intermediate proliferative stage.

Figure 5A:
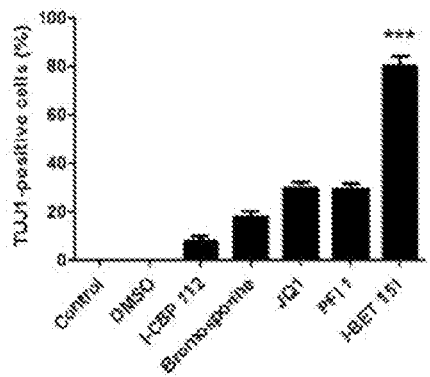
FIGS. 5A-C show the effect of FSK, CHIR and I-BET151 on inducing TUJ1 positive cells compared with their functional substitutions. Control, not induced; DMSO, vehicle control. The data are presented as the mean+/−SEM. *P<0.05; ***P<0.001 (Student's t-test).
Figure 5B:
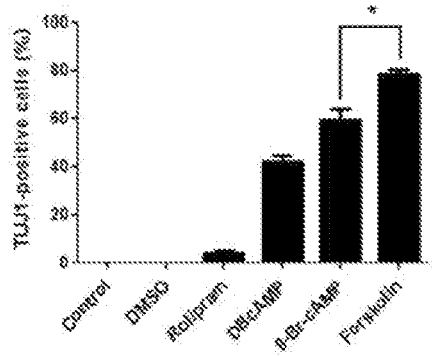
Figure 5C:
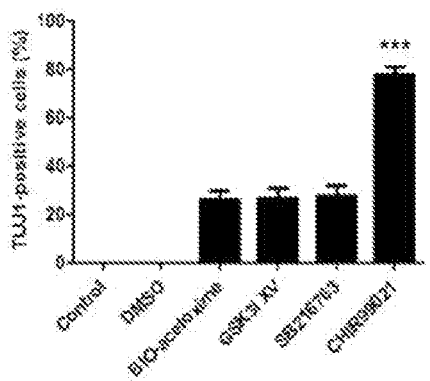

Small Molecules Directly Induced the Activation of Neuronal-Master Transcription Factors and the Silencing of Fibroblast-Specific Genes During CiNs Generation To explore the roles of the small molecules in chemical reprogramming their biological activity was first investigated by replacing the individual small molecule with their functional substitutions. The data shows that Forskolin (a cAMP agonist), CHIR99021 (a GSK3 inhibitor) and I-BET151 (a BET family bromodomain inhibitor) could be substitute by other cAMP agonists, GSK3 inhibitors and BET inhibitors, respectively (FIG. 5A-C), suggesting their functional targets in chemical reprogramming into CiNs.

Figure 5D:
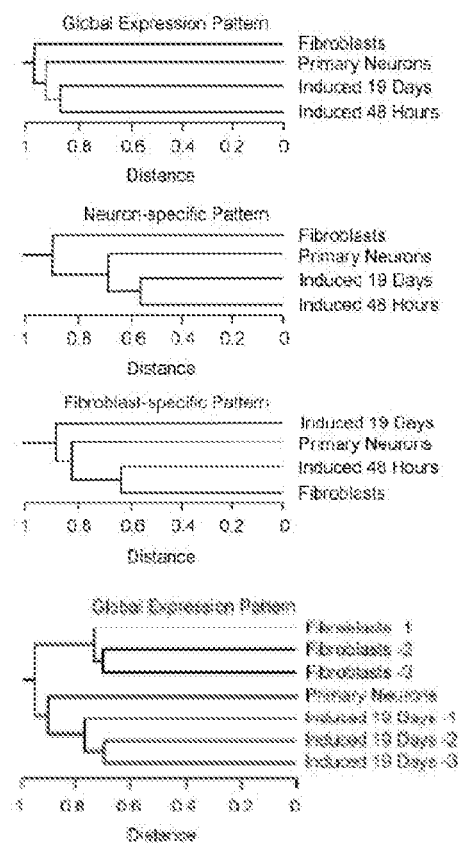
FIGS. 5D and 5E show hierarchical clustering (FIG. 5D) and the degree of overlapping expression (FIG. 5E) among fibroblasts, small-molecule induced fibroblasts and primary neurons.
Figure 5E:
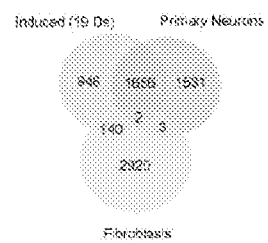
Figure 5F:
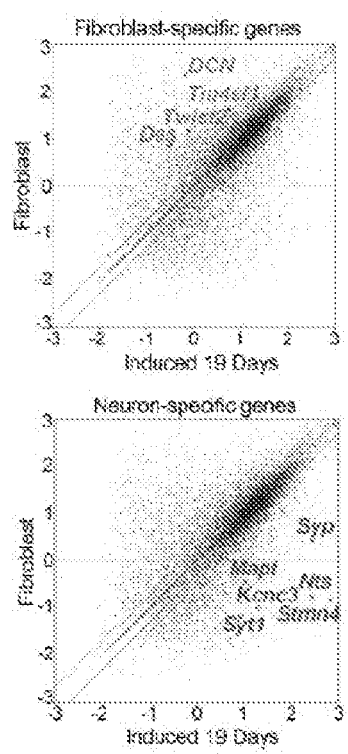
FIG. 5F includes scatter plots which show that multiple neuronal signature genes are increased (lower panel), whereas fibroblasts genes are suppressed after chemical treatment (top panel).
Figure 5G:
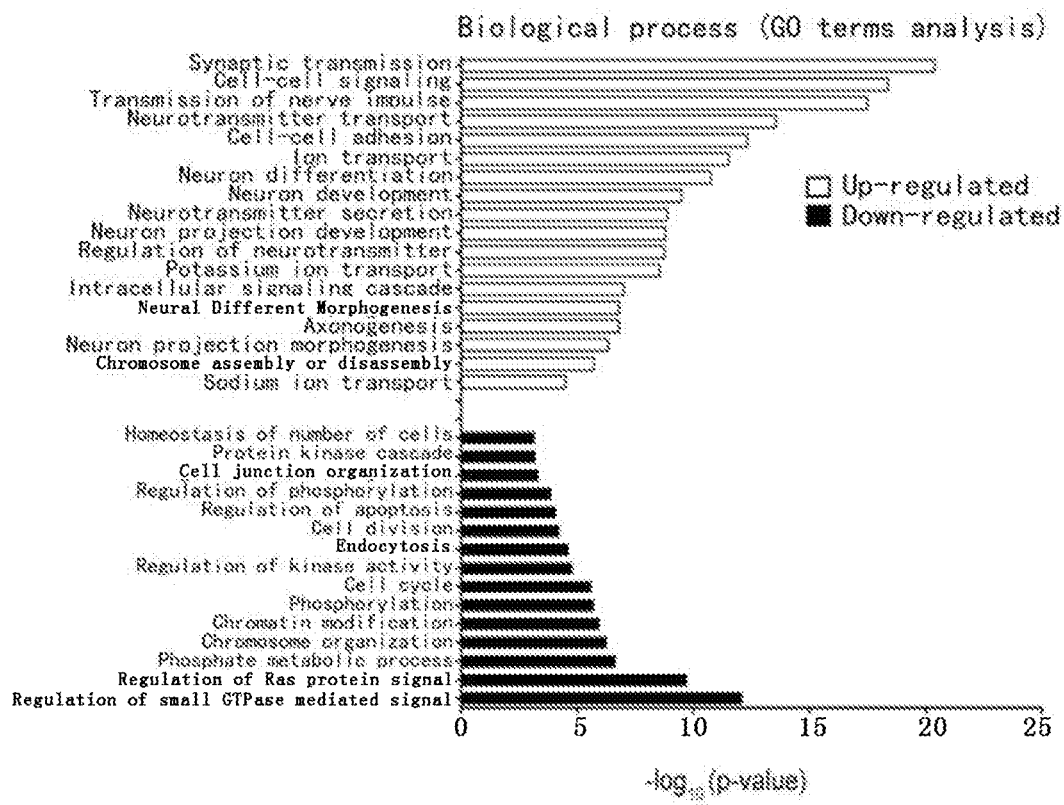
FIG. 5G shows gene ontology (GO) analysis of the mainly enriched genes after chemical induction.

To further characterize the process of cell fate reprogramming from the perspective of endogenous mastering transcriptional factors, changes in expression of endogenous transcriptional networks induced by small molecules. RNA-Seq analysis was carried out to examine the change of global expression profiling after treatment with small molecules for 48 hours and 19 days. As demonstrated by hierarchical clustering, the induced cells grouped closely to the primary neurons, but distinctly from the fibroblasts (FIG. 5D). Accordingly, by selecting the genes differently expressed at least three-fold among fibroblast, CiNs and primary neurons, (Caiazzo, et al., *Nature*, 476:224-227 (2011); Du, et al., *Cell Stem Cell*, 14:394-403 (2014), the general degree of overlapping and differentially-expressed genes showed similarities between the cells after induction and primary neurons (FIG. 5D, bottom panel, and FIG. 5E). Compared to the fibroblasts, the cells at 19 days post treatment enriched the expression of multiple neuronal-specific genes, including the genes involving in neuronal morphogenesis and maintenance, ion channels and functional synaptic components (Mapt (microtubule-associated protein tau), Gap43 (growth associated protein 43), Stmn3 (stathmin-like 3), Stmn4, Syn1 (synapsin 1), Syp (synaptophysin) and Syt1 (synaptotagmin 1)) (data not shown). The expression of other genes such as Nef1 (neurofilament light polypeptide), Nrxn2 (neurexin2), Nsg2 (neuron specific gene family member 2), Cacna1b (calcium channel alpha 1b subunit), kcnc3 (Potassium voltage-gated channel subfamily C member 3), slc32a1 (Vesicular inhibitory amino acid transporter; solute carrier family 32), gad (glutamate decarboxylase)1, gad2, Gria2 (glutamate receptor 2), Gria4, Ache (acetylcholinesterase), Drd2 (dopamine receptor D2), Kcnj11 (potassium inwardly rectifying channel subfamily J, member 11), Ppp1r1b (Protein phosphatase 1 regulatory subunit 1B), Snca (synuclein alpha) and Syngr3 (synatogyrin 3) were also enriched. (FIG. 5F). Furthermore, the expression of fibroblast hallmark genes (Fap, Des, Twist2 and others) was down-regulated (data not shown) (Caiazzo et al., *Nature*, 476:224-227 (2011); Kim et al., *Cell Stem Cell*, 9:413-419 (2011)), indicating the loss of the original fibroblast features in CiNs. Consistently, Analysis of the genes differentially expressed >10 fold showed that the expression of fibroblasts enriched genes were disrupted in the small molecule treated cells, while neuron enriched genes were up-regulated in these cells. After 19 days of chemical induction, 60.6% of neuron-enriched genes were up-regulated by more than 2 fold, while only 1.8% of these genes were down-regulated (data not shown). Furthermore, 80% of the fibroblast enriched genes were down-regulated by at least 2 fold, whereas only 6.1% were up-regulated (data not shown), indicating that the small-molecule induction has the dual effect of activating global neuron-enriched genes and suppressing global fibroblast-enriched genes. GO (Gene Ontology) analysis showed the up-regulated genes after chemical induction were mainly enriched in synaptic transmission, neuron differentiation, neuron development, ion transport, axonogenesis, ion channel activities and other crucial biological process in neural development. The down-regulated genes mainly participate in biological processes like cell cycle, cell division and others (FIG. 5G). Taken together, these results indicate that the cells obtained following small-molecule induction gained a transcriptional profile resembling primary neurons, whereas the transcriptional the program of the original cells was down-regulated.

Figure 6A:
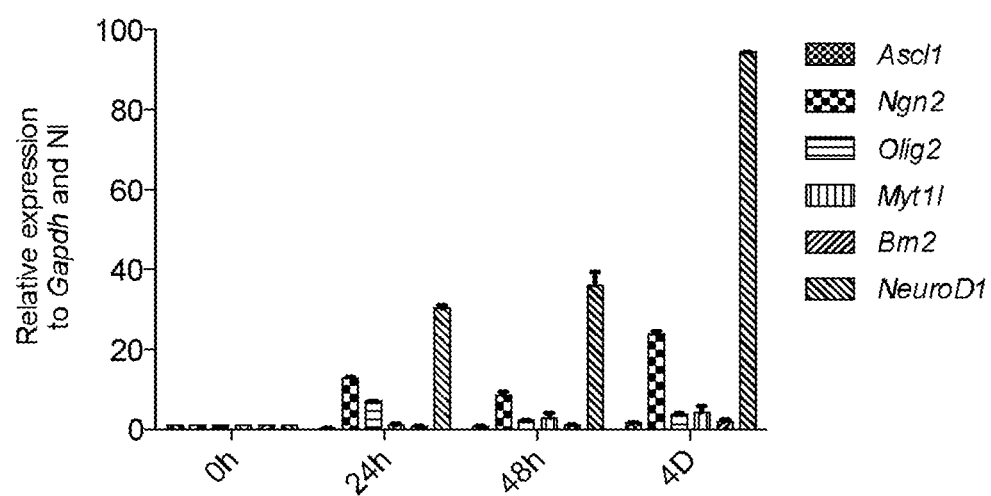
FIGS. 6A-6G show the roadmap of chemical reprogramming.
Figure 6B:
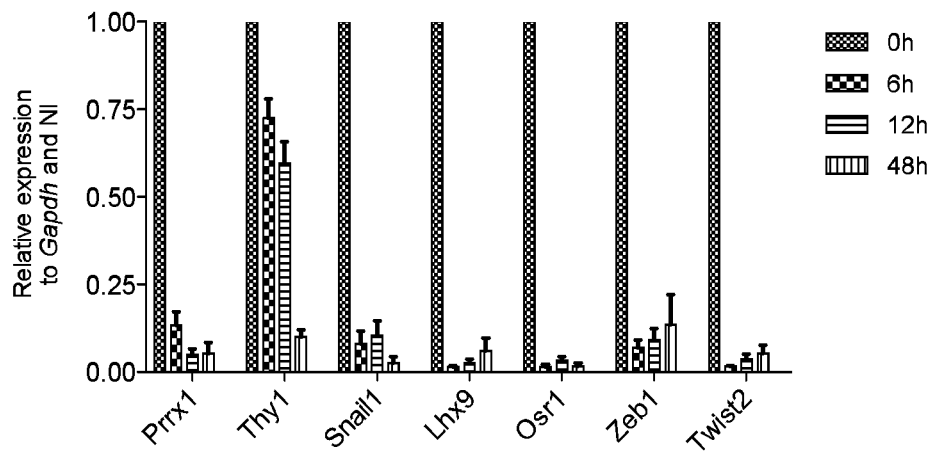
Figure 6C:
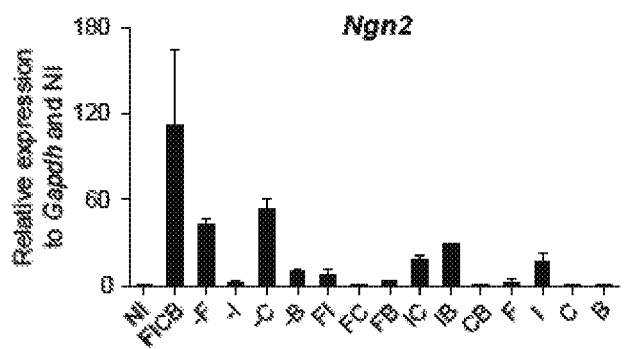
Figure 6D:
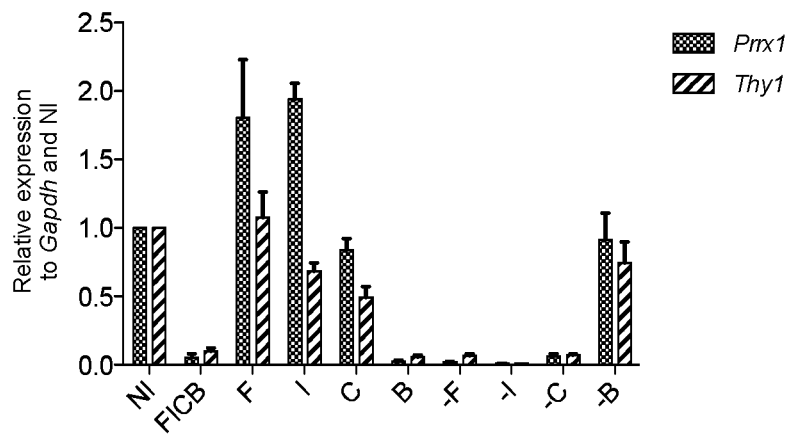
Figure 6E:
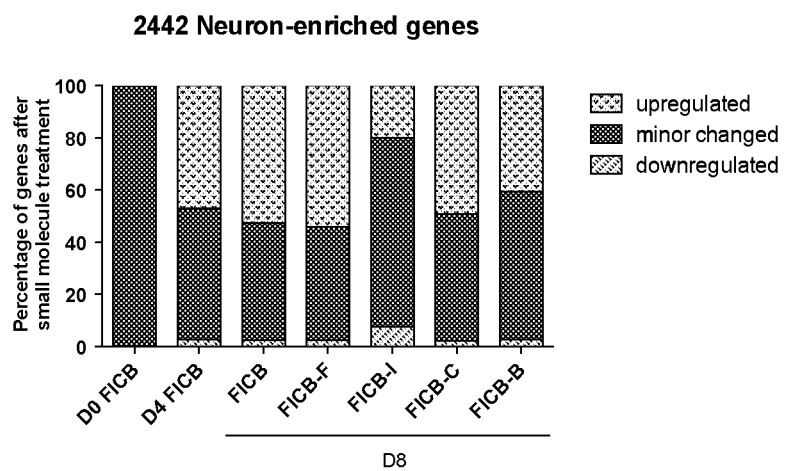
Figure 6F:
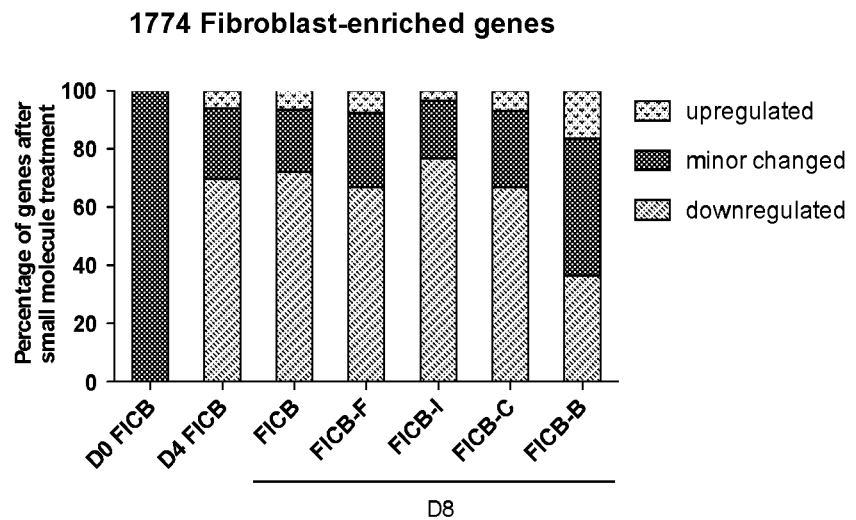
Figure 6G:
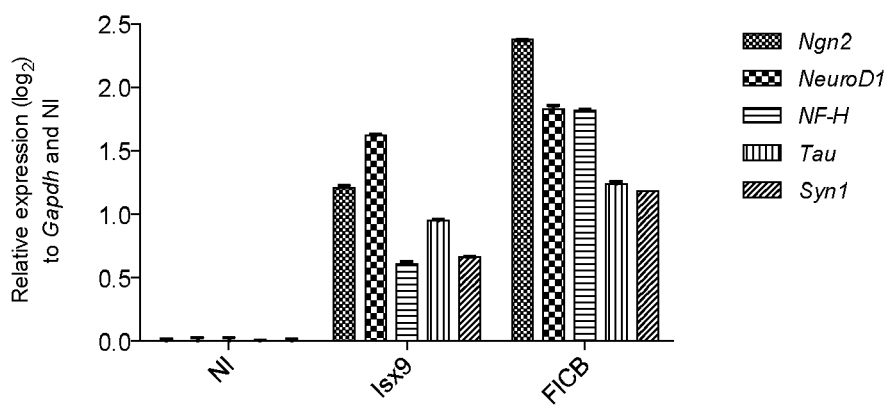

RT-qPCR analysis showed that the activation of the neural-fate-determining and the down-regulation of fibroblast-fate-determining factors were induced within 24 hours (FIGS. 6A and 6B). ISX9 is necessary for activation of multiple neuron-specific genes, including the neuron-mastering genes such as NeuriD1 (FIG. 6G). In the phase of 48 hour-chemical induction, the expression of NeuroD1 and Ngn2, two neural-fate mastering genes, was dramatically induced (FIGS. 6A and 6C), suggesting that these two transcription factors may be involved in the first step of chemical reprogramming. Surprisingly, Ascl1, the master transcription factor most frequently used to induce neuronal fate conversion was not activated in the early stage of reprogramming (FIG. 6A).

Next, the roles of the small molecules in regulating these endogenous cell-fate-determining factors were determined. By removing each small molecule from the cocktail, ISX9 was identified as essential to induce the master neural genes (FIGS. 6C and 6D and 6G). The data also shows that I-BET151 was the core small molecule to suppress the endogenous fibroblast-fate-determining program (FIGS. 6E and 6F), which accounts for an efficient disruption of the fibroblast core transcriptional network by chemicals. These results indicate that the cell fate was manipulated by small molecules through synergistically activating the target cell-fate-mastering program and repressing the initial cell-fate-mastering program.

Chemical Induction of Functional Neurons from Mouse Astrocytes

This example demonstrates use of the same 4 small-molecule cocktail used to induce mouse fibroblasts into functional neurons, to induce mouse astrocytes into functional neurons.

To generate functional neurons from mouse astrocytes, mouse astrocytes were isolated as described above, and the isolated mouse astrocytes were induced by neuronal induction medium (containing Neurobasal Media, 1% N2 and 2% B27 supplements, 1% GlutaMAX, 1% penicillin-streptomycin and bFGF, 100 ng/mL) plus the four chemical molecules (FICB) for 12-16 days and then cultured for 12 days in maturation medium (described above for fibroblasts).

Figure 7A:
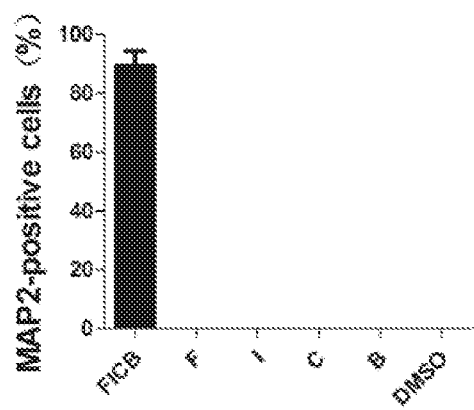
FIG. 7A is a bar graph showing quantification of MAP-2 positive cells induced by IFCB, or by addition individual agents from the cocktail.
Figure 7B:
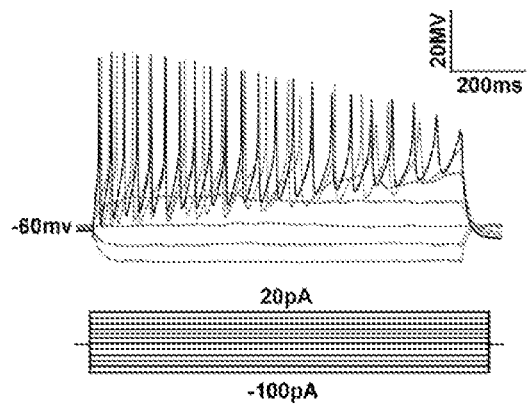
FIG. 7B shows whole-cell voltage-clamp recordings of CiNs cultured in maturation medium for 12 days.

Cells were harvested at different time points and expression of various markers measured to determine progression of chemical induction. Before chemical induction, astrocytes expressed the typical astrocyte marker GFAP (data not shown). After chemical treatment, the induced cells expressed typical neuronal markers (TUJ1, MAP-2, Syn1 and GABA; data not shown) and the induction was robust (>80% MAP2-positive cells can be generated) (FIG. 7A). Furthermore, the combination of the four small molecules is necessary to induce neuronal cells from mouse astrocytes (FIG. 7A). Each small molecule alone failed to generate neuronal-like cells as measured by MAP-2-positive cells, suggesting a synergism between the small molecules may be crucial. The induced cells fired action potential, showing mature neuronal functional properties (FIG. 7B).

These findings show that the novel small-molecule cocktail can initiate neuronal fates in cells other than fibroblasts.

DISCUSSION

Novel cocktails of small molecules that induce an efficient direct lineage reprogramming across germ layers from fibroblasts into functional neurons have been identified. The chemically-induced neurons possess neuronal properties with respect to gene expression pattern and electrophysiological functional capabilities. These findings demonstrate that somatic cell fates can be converted from one terminally differentiated cell type to another by manipulating cell signaling pathways and endogenous cell-fate-determining programs with pure small molecules, without the need of exogenous transgenes or other cell fate-specific factors, such as microRNAs.

Although the master transcription factors are considered as the major determinants of specific cell identities (Xu et al., *Cell Stem Cell*, 16:119-134 (2015), the data in this application show that a small molecule cocktail is sufficient to activate the expression of such genes. As shown in these studies, ISX9, an isoxazole, which has been shown to facilitate neural differentiation via a neurotransmitter-evoked Ca signal (Schneideret, al., *Nat Chem Biol.*, 4:408-410 (2008)), induced the activation of neuronal genes in fibroblasts, which was further enhanced by other small molecules (FIGS. 6C and 6G). For inducing CiNs, Ngn2 and NeuroD1 were the first-wave responsive genes in the reprogramming process, which can be activated within 6 hours (FIG. 6A). Recently, Ngn2, the neuron-fate-determining proneural gene in development, has been demonstrated to be capable of establishing neuronal cell fate with additional transcriptional factors or small molecules (Liu et al., *Nat Commun.*, 4:2183 (2013); Bertrand, et al., *Nat Rev. Neurosci.*, 3:517-530 (2002)). Other neural factors were sequentially activated in the following days. This suggests that the small molecule-driven fibroblast-to-neuron direct reprogramming is a hierarchical transcriptional activation process, in which the efficient activation of cell-fate-determining genes by small molecules may initiate and stabilize an auto-regulatory loop of the neuronal-specific transcriptional program, and may further stimulate the expression of downstream regulatory genes and establish the neuronal functional properties.

The addition of I-BET151 into the small molecule cocktail significantly improved the reprogramming process (data not shown and FIG. 2B). Further, I-BET151 was identified as a key small molecule down-regulating the fibroblast core transcriptional network (FIG. 6D). I-BET151 is reported to competitively bind at the BRD domain of BET family proteins (Seal et al., *Bioorg Med Chem Lett.*, 22:2968-29722012)). BRD4, a BET family protein, was reported to specifically bind to the activated chromatin domains and maintain the cell fate-specific gene expression pattern (Wu et al, *Cell Stem Cell*, 4(3):390-403(2015)). The inhibition of BRD4 may disrupt the cell fate maintenance and alter the gene expression pattern of the initial cell type (Chiang et al., *Chem Biol.*, 21:804-806 (2014); Di Micco et al., *Cell Rep.*, 9:234-247 (2014)), which is consistent with the finding that I-BET 151 directly disrupts the fibroblast-specific gene expression program in early stage reprogramming (FIGS. 6D and 6F). This finding is consistent with the "mutual repression model" in cell fate conversion (Wang et al., *Proc Natl Acad Sci USA,* 108:8257-82622011) and the previous findings that cell fate reprogramming could be facilitated by knockdown of key transcription factors in the initial cell type (Hanna et al., *Cell*, 133:250-264 (2008)). Recent studies show that BRD4 binds to super-enhancers of core genes to maintain the pluripotent cell fate of ESCs, whereas inhibition of BRD4 results in losing the core program of ESCs and committing to neuroectodermal lineage (Di Micco et al., *Cell Rep.,* 9:234-247 (2014). It is possible that small molecules targeting protein complexes at super-enhancers or related to active gene expression may contribute to cell lineage reprogramming as a general eraser of initial cell identities in the future.

Overall, these studies show that small molecule cocktails can be used to manipulate cell fates by replacing reported lineage reprogramming genes, activating desirable cell type-specific master gene expression and silencing initial cell type-specific master gene expression. The strategy of chemical reprogramming disclosed here can be used to manipulate human somatic cell fates.

We claim:

1. A composition for inducing non-neural eukaryotic cells to possess neuron-like properties, the composition comprising: chemical inducers of neuron-like properties (CINPs) comprising: a first concentration of at least one cyclic AMP (cAMP) agonist; a second concentration of a neurogenic small molecule which is N-Cyclopropyl-5-(2-thienyl)-3-isoxazolecarboxamide (ISX9 or "I"); a third concentration of at least one glycogen synthase kinase (GSK) inhibitor; a fourth concentration of at least one TGFβ receptor inhibitor; and a fifth concentration of at least one BET family bromodomain inhibitor, such that the first, second, third, fourth, and fifth concentrations of the CINPs are effective to induce reprogramming of the non-neuronal eukaryotic cells into neuron-like cells.

2. The composition of claim 1, wherein the at least one cAMP agonist is selected from the group consisting of rolipram, DBc-AMP (Dibutyryl-cAMP), 8-Bromo-cAMP and Forskolin ("F"), and combinations thereof, and wherein the first concentration of the at least one cAMP agonist ranges from 50 µM to 100 µM.

3. The composition of claim 1, wherein the second concentration of the at least one neurogenic small molecule ranges from 10 µM to 20 µM.

4. The composition of claim 1, wherein the GSK inhibitor is selected from the group consisting CHIR99021 ("C") [6-[[2-[[4-(2,4-Dichlorophenyl)-5-(5-methyl-1H-imidazol-2-yl)-2-pyrimidinyl]amino]ethyl]amino]-3-pyridinecarbonitrile], SB216763 [3-(2,4-Dichlorophenyl)-4-(1-methyl-1H-indol-3-yl)-1H-pyrrole-2,5-dione)], GSK 3I XV, Bio-acetoxime [(2'Z,3'E)-6-Bromoindirubin-3'-acetoxime], and combinations thereof, and wherein the third concentration of the at least one GSK inhibitor ranges from 10 µM to 20 µM.

5. The composition of claim 1, wherein the fourth concentration ranges from 2 µM to 10 µM.

6. The composition of claim 5, wherein the at least one TGF β inhibitor comprises SB431542 ("S") [4-[4-(1,3-benzodioxol-5-yl)-5-(2-pyridinyl)-1H-imidazol-2-yl]benzamide].

7. The composition of claim 1, wherein the at least one BET family bromodomain inhibitors is selected from the group consisting of I-BET151 ("B") [(7-(3,5-dimethylisoxazol-4-yl)-8-methoxy-1-((R)-1-(pyridin-2-yl)ethyl)-1H-imidazo[4,5-c]quinolin-2(3H)-one]; JQ1 [(6S)-4-(4-Chlorophenyl)-2,3,9-trimethyl-6H-thieno[3,2-f][1,2,4]triazolo[4,3-a][1,4]diazepine-6-acetic acid 1,1-dimethylethyl ester]; Bromosporine; and I-CBP112 [1-[7-(3,4-Dimethoxyphenyl)-9-[[(3S)-1-methylpiperidin-3-yl]methoxy]-2,3,4,5-tetrahydro-1,4-benzoxazepin-4-yl]propan-1-one], and combinations thereof, and wherein the fifth concentration ranges from 2 µM to 10 µM.

8. The composition of claim 7, wherein the BET family bromodomain inhibitor is I-BET151 ("B") [(7-(3,5-dimethylisoxazol-4-yl)-8-methoxy-1-((R)-1-(pyridin-2-yl)ethyl)-1H-imidazo[4,5-c]quinolin-2(3H)-one).

9. The composition of claim 1, wherein the one or more chemical inducers of neuron-like properties (CINPs) comprises:
Forskolin ("F");
ISX9 ("I") [N-Cyclopropyl-5-(2-thienyl)-3-isoxazolecarboxamide];
CHIR99021 ("C") [6-[[2-[[4-(2,4-Dichlorophenyl)-5-(5-methyl-1H-imidazol-2-yl)-2-pyrimidinyl]amino]ethyl]amino]-3-pyridinecarbonitrile]; and
SB431542 ("S") [4-[4-(1,3-benzodioxol-5-yl)-5-(2-pyridinyl)-1H-imidazol-2-yl]benzamide].

10. The composition of claim 1, wherein the one or more chemical inducers of neuron-like properties (CINPs) comprises
Forskolin ("F");
ISX9 ("I") [N-Cyclopropyl-5-(2-thienyl)-3-isoxazolecarboxamide];
CHIR99021 ("C") [6-[[2-[[4-(2,4-Dichlorophenyl)-5-(5-methyl-1H-imidazol-2-yl)-2-pyrimidinyl]amino]ethyl]amino]-3-pyridinecarbonitrile]; and
I-BET151 ("B") [(7-(3,5-dimethylisoxazol-4-yl)-8-methoxy-1-((R)-1-(pyridin-2-yl)ethyl)-1H-imidazo[4,5-c]quinolin-2(3H)-one).

11. The composition of claim 1, further comprising:
an inhibitor selected from the group consisting of a selective inhibitor of Rho-associated, coiled-coil containing protein kinase (ROCK), a p38 mitogen activated kinase (MAPK) inhibitor, and combinations thereof.

12. The composition of claim 1, further comprising:
one or more compounds selected from the group consisting of Y27632 [(+)-(R)-trans-4-(1-aminoethyl)-N-(4-pyridyl) cyclohexanecarboxamide+++dihydrochloride)], Fusadil, BIRB796 (Doramapimod), SB203580 (4-(4'-Fluorophenyl)-2-(4'-methylsulfinylphenyl)-5-(4'-pyridyl)-imidazole), and combinations thereof, and each at a concentration ranging from 0.5 µM to 5 µM.

13. The composition of claim 1, wherein the CINPs are effective to induce neuron-like properties in the non-neuronal eukaryotic cells, wherein the neuron-like properties are selected from the group consisting of neuronal morphology, membrane depolarization as measured by a patch clam assay, expression of one or more markers selected from the group consisting of TUJ1, MAP2, NF-H, NeuN, vGlut, Gad67, and combinations thereof.

14. The composition of claim 1, wherein the non-neuronal eukaryotic cells comprise fibroblast cells.

* * * * *